US012584176B2

(12) United States Patent
Venkat et al.

(10) Patent No.: US 12,584,176 B2
(45) Date of Patent: *Mar. 24, 2026

(54) INTEGRATED MACHINE-LEARNING FRAMEWORK TO ESTIMATE HOMOLOGOUS RECOMBINATION DEFICIENCY

(71) Applicant: Tempus AI, Inc., Chicago, IL (US)

(72) Inventors: Aarti Venkat, Chicago, IL (US); Jerod Parsons, Chicago, IL (US); Joshua SK Bell, Chicago, IL (US); Catherine Igartua, Chicago, IL (US); Yilin Zhang, Wilmette, IL (US); Ameen Salahudeen, Oak Park, IL (US); Verönica Sänchez Freire, Chicago, IL (US); Robert Tell, Chicago, IL (US)

(73) Assignee: Tempus AI, Inc., Chicago, IL (US)

( * ) Notice: Subject to any disclaimer, the term of this patent is extended or adjusted under 35 U.S.C. 154(b) by 943 days.

This patent is subject to a terminal disclaimer.

(21) Appl. No.: 17/150,615

(22) Filed: Jan. 15, 2021

(65) Prior Publication Data

US 2021/0246511 A1     Aug. 12, 2021

Related U.S. Application Data

(63) Continuation of application No. 16/789,363, filed on Feb. 12, 2020, now Pat. No. 10,975,445.

(60) Provisional application No. 62/946,347, filed on Dec. 10, 2019, provisional application No. 62/804,730, filed on Feb. 12, 2019.

(51) Int. Cl.
| | |
|---|---|
| *C12Q 1/6886* | (2018.01) |
| *G06F 17/18* | (2006.01) |
| *G06N 3/02* | (2006.01) |
| *G16B 20/00* | (2019.01) |
| *G16B 40/00* | (2019.01) |
| *G16B 50/30* | (2019.01) |

(52) U.S. Cl.
CPC ........... *C12Q 1/6886* (2013.01); *G06F 17/18* (2013.01); *G06N 3/02* (2013.01); *G16B 20/00* (2019.02); *G16B 40/00* (2019.02); *G16B 50/30* (2019.02)

(58) Field of Classification Search
CPC ...... C12Q 1/6886; G16B 50/30; G16B 40/00; G16B 20/00; G06F 17/18; G06N 3/02
See application file for complete search history.

(56) References Cited

U.S. PATENT DOCUMENTS

| | | |
|---|---|---|
| 2013/0029926 A1 | 1/2013 | Timms et al. |
| 2017/0283879 A1 | 10/2017 | Abkevich et al. |
| 2018/0030544 A1 | 2/2018 | Abkevich et al. |

FOREIGN PATENT DOCUMENTS

| | | |
|---|---|---|
| CN | 113257346 A | 8/2021 |
| JP | 2017-21299 A | 12/2017 |
| JP | 2019-519872 A | 7/2019 |
| WO | WO 2017/165270 A1 | 9/2017 |
| WO | WO 2017/178509 A1 | 10/2017 |

OTHER PUBLICATIONS

Belli, et al. "Homologous recombination deficiency in triple negative breast cancer," The Breast, 45, pp. 15-21 (2019).

Bonadio, et al. "Homologous recombination deficiency in ovarian cancer: a review of its epidemiology and management," Clinics, pp. 1-6 (2018).

Chang, et al. "Homologous recombination deficiency (HRD) by BROCA-HR and survival outcomes after surgery for patients (pts) with pancreatic adenocarcinoma (Pc): A single institution experience," Journal of Clinical Oncology, 38, No. 4, pp. 1-3 (Feb. 4, 2020).

Coleman, et al. "Rucaparib maintenance treatment for recurrent ovarian carcinoma after response to platinum therapy (ARIEL3): a randomised, double-blind, placebo-controlled, phase 3 trial," Lancet. Author manuscript; available in PMC, pp. 1-26 (Apr. 16, 2018).

Criscuolo, et al. "New combinatorial strategies to improve the PARP inhibitors efficacy in the urothelial bladder Cancer treatment," Journal of Experimental & Clinical Cancer Research, pp. 1-9 (2019).

Davies, et al. "HRDetect is a predictor of BRCA1 and BRCA2 deficiency based on mutational-signatures," Nat. Med., pp. 1-28 (2017).

Fogelman, et al. "Evidence for the Efficacy of Iniparib, a PARP-1 Inhibitor, in BRCA2-associated Pancreatic Cancer," Anticancer Research, 31, pp. 1417-1420 (2011).

Gulhan, et al. "Detecting the mutational signature of homologous recombination deficiency in clinical samples," nature genetics, vol. 51, pp. 912-922 (May 2019).

(Continued)

*Primary Examiner* — Jerry Lin

(74) *Attorney, Agent, or Firm* — MORGAN, LEWIS & BOCKIUS LLP

(57) ABSTRACT

Methods, systems, and software are provided for determining a homologous recombination pathway status of a cancer in a test subject, e.g., to improve cancer treatment predictions and outcomes. In some embodiments, classifiers using one or more of (i) a heterozygosity status for DNA damage repair genes in a cancerous tissue, (ii) a measure of the loss of heterozygosity across the genome of the cancerous tissue, (iii) a measure of variant alleles detected in a second plurality of DNA damage repair genes in the genome of the cancerous tissue, (iv) a measure of variant alleles detected in the second plurality of DNA damage repair genes in the genome of a non-cancerous tissue, and (v) tumor sample purity are provided.

25 Claims, 13 Drawing Sheets

Specification includes a Sequence Listing.

(56)     References Cited

OTHER PUBLICATIONS

Heeke, et al. "Prevalence of Homologous Recombination-Related Gene Mutations Across Multiple Cancer Types," JCO Precis Oncol., pp. 1-18, (2018).
Helfand, "ESMO: AZ, Merck's Lynparza brings precision medicine to prostate cancer with 'game-changer' results," FiercePharma, pp. 1-6 (Sep. 30, 2019).
Hodgson, et al. "Candidate biomarkers of PARP inhibitor sensitivity in ovarian cancer beyond the BRCA genes," British Journal of Cancer, pp. 1401-1409 (2018).
Hoppe, et al. "Biomarkers for Homologous Recombination Deficiency in Cancer," JNCI J Natl Cancer Inst 110 (7), pp. 704-713 (May 18, 2018).
Kausar, et al. "Sensitization of Pancreatic Cancers to Gemcitabine Chemoradiation by WEE1 Kinase Inhibition Depends on Homologous Recombination Repair," NEOPLASIA, vol. 17, No. 10, pp. 757-766 (Oct. 2015).
Knijnenburg, et al. "Genomic and Molecular Landscape of DNA Damage Repair Deficiency across The Cancer Genome Atlas," Cell Reports, pp. 1-23 (2018).
Longo, "Personalized Medicine for Primary Treatment of Serous Ovarian Cancer," The New England Journal of Medicine, 381, 25, pp. 2471-2474 (Dec. 19, 2019).
Marquard, et al. "Abstract 2822: A pan-cancer analysis of inferred homologous recombination deficiency identifies potential platinum benefit in novel subtypes," American Associate for Cancer Research, pp. 1-4 (Oct. 2014).
Mateo, et al. "DNA-Repair Defects and Olaparib in Metastatic Prostate Cancer," The New England Journal of Medicine, vol. 373, No. 18, pp. 1697-1708 (Oct. 29, 2015).
Mirza, et al. "Niraparib Maintenance Therapy in Platinum-Sensitive, Recurrent Ovarian Cancer," The New England Journal of Medicine, pp. 2154-2164 (Oct. 8, 2016).
Naipal, et al. "Functional Ex Vivo Assay to Select Homologous Recombination-Deficient Breast Tumors for PARP Inhibitor Treatment," Clinical Cancer Research, pp. 4816-4827 (Sep. 15, 2014).
Nguyen, et al. "Pan-cancer landscape of homologous recombination deficiency," bioRxiv, http://dx.doi.org/10.1101/2020.01.13.905026, pp. 1-32 (Jan. 14, 2020).
O'Kane, et al. "Homologous recombination deficiency (HRD) scoring in pancreatic ductal adenocarcinoma (PDAC) and response to chemotherapy," Journal of Clinical Oncology, 38, pp. 1-2 (Feb. 1, 2020).
Pokataev, et al. "Efficacy of platinum-based chemotherapy and prognosis of patients with pancreatic cancer with homologous recombination deficiency: comparative analysis of published clinical studies," ESMO Open Cancer Horizons, pp. 1-8 (Jan. 29, 2020).
Stronach, "Biomarker Assessment of HR Deficiency, Tumor BRCA1/2 Mutations, and CNE1 Copy Number in Ovarian Cancer: Associations with Clinical Outcome Following Platinum Monotherapy," American Association for Cancer Research, pp. 1103-1112 (2018).
Sztupinszki, et al. "Detection of molecular signatures of homologous recombination deficiency in prostate cancer with or without BRCA1/2 mutations Running title: Homologous recombination deficiency in prostate cancer," Clinical Cancer Research, pp. 1-29 (Feb. 18, 2020).
Takaya, et al. "Homologous recombination deficiency status-based classification of high-grade serous ovarian carcinoma," Scientific Reports, pp. 1-8 (2020).
Teo, et al. "Is it time to split strategies to treat homologous recombinant deficiency in pancreas cancer?", Journal of Gastrointestinal Oncology, pp. 738-749 (2016).
Telli, et al. "Homologous Recombination Deficiency (HRD) Score Predicts Response to Platinum-Containing Neoadjuvant Chemotherapy in Patients with Triple-Negative Breast Cancer," Clinical Cancer Research, 22(15), pp. 3764-3774 (Aug. 1, 2016).
Timms, et al. "Association of BRCA1/2 defects with genomic scores predictive of DNA damage repair deficiency among breast cancer subtypes," Breast Cancer Research, pp. 1-9 (2014).

Vencken, et al. "Chemosensitivity and outcome of BRCA1- and BRCA2- associated ovarian cancer patients after first-line chemotherapy compared with sporadic ovarian cancer patients," Annals of Oncology 22: pp. 1346-1352 (2011).
Zhao, et al. "Homologous Recombination Deficiency and Platinum-Based Therapy Outcomes in Advanced Breast Cancer," Clinical Cancer Research, pp. 7521-7531 (Dec. 15, 2017).
Breakthrough From PAOLA1 GINECO/ENGOT-OV25 Trial: Adding Olaparib To Bevacizumab Maintenance Demonstrates Substantial Clinical Benefit in Newly Diagnosed Advanced Ovarian Cancer, ESMO, pp. 1-3 (Sep. 28, 2019).
ESMO 2019—Clovis is running out of waves to catch, Vantage, pp. 1-3 (Oct. 1, 2019).
Incorporating Veliparib Into Chemotherapy and Continuing With Veliparib Maintenance Significantly Improved PFS in Newly Diagnosed High-Grade Serous Ovarian Cancer, ESMO, pp. 1-3 (Sep. 28, 2019).
Label: Lynparza—olaparib tablet, film coated, pp. 1-42 (Dec. 27, 2019).
Lynparza achieved a 72% objective response rate in patients with relapsed, germline BRCAmutated advanced ovarian cancer, pp. 1-4 (Jun. 3, 2019).
Myriad Genetics myChoice HRD® Update, pp. 1-24 (Jun. 30, 2016).
Myriad myChoice® HRD—Technical Specifications, (2017) pp. 1-3.
Myriad Files sPMA With FDA for Test to ID Best Responders to Lynparza, Avastin Combination, genomeweb, pp. 1-2 (Feb. 11, 2020).
Niraparib Prolongs PFS in Patients With Newly Diagnosed Advanced Ovarian Cancer, ESMO, pp. 1-3 (Sep. 28, 2019).
Phase III PROfound Study Evaluates Olaparib in Setting of Metastatic, Castration-Resistant Prostate Cancer, ESMO, pp. 1-5 (Nov. 10, 2019).
TESARO Announces Expansion to Second Stage of JASPER Trial of ZEJULAR in Combination With TSR-042 in Non-Small Cell Lung Cancer, pp. 1-5 (Sep. 10, 2018).
The role of PARP-1 in the repair of single stranded break (SSB), Novus Biologicals a biotechne brand, pp. 1-2 (Apr. 22, 2016).
Aguilera, Andres, et al. "Transcription and Recombination: When RNA Meets DNA," Cold Spring Harbor Perspect Biol, 2014, pp. 17.
Abkevich et al. 2012 Patterns of genomic loss of heterozygosity predict homologous recombination repair defects in epithelial ovarian cancer British Journal of Cancer vol. 107, pp. 1776-1782 (Year: 2012).
Ha, Gavin, et al. "Integrative analysis of genome-wide loss of heterozygosity and mono-allelic expression at nucleotide resolution reveals disrupted pathways in triple negative breast cancer", http://genome.cship.org/subscriptions, Cold Spring Harbor Laboratory Press, May 21, 2012, pp. 1-38.
Kawazu, Masahito et al. "Integrative analysis of genomic alterations in triple-negative breast cancer in association with homologous recombination deficiency," PLOS Genetics, 13(6), Jun. 21, 2017, pp. 1-23.
Konstantinopoulos et al. Gene Expression Profile of BRCAness That Correlates With Responsiveness to Chemotherapy and With Outcome in Patients With Epithelial Ovarian Cancer Journal of Clinical Oncology vol. 28, pp. 3555-3561 (Year: 2010).
Lu et al. Correlation between gene expression and mutator phenotype predicts homologous recombination deficiency and outcome in ovarian cancer Journal of Molecular Medicine vol. 92, pp. 1159-1168 (Year: 2014).
McDevitt, Shane, et al. "How RNA transcripts coordinate DNA recombination and repair," Nature Communications, 2018, 9:1091, pp. 10.
Peng, Guang, et al. "Genome-wide Transcriptome Profiling of Homologous Recombination DNA Repair," Nat Commun. Author manuscript, Jul. 1, 2014, pp. 21.
Subramanian et al. Gene set enrichment analysis: A knowledge-based approach for interpreting genome-wide expression profiles Proceedings of the National Academy of Sciences USA vol. 102, pp. 15545-15550 (Year: 2005).

(56)            References Cited

OTHER PUBLICATIONS

Tomczak et al. The Cancer Genome Atlas (TCGA) an immeasurable source of knowledge Contemporary Oncology vol. 19, pp. A68-A77 (Year: 2015).

Bengtsson, Henrik et al., "TumorBoost: Normalization of allele-specific tumor copy numbers from a single pair of tumor-normal genotyping microarrays", BMC Bioinformatics, Biomed Central, London, GB, vol. 11, No. 1, May 12, 2010 (May 12, 2010), p. 245.

Santana Dos Santos, Elizabeth et al., "Non-Coding Variants in BRCA1 and BRCA2 Genes: Potential Impact on Breast and Ovarian Cancer Predisposition", Cancers, vol. 10, No. 11, Nov. 16, 2018 (Nov. 16, 2018), p. 453.

Broderick, "BRCA Mutations Linked to Longer Survival in Ovarian Cancer," (2016), Society of Gynecologic Oncology (SGO) Annual Meeting, pp. 1-2.

Caffrey, "Myriad Genetics Submits myChoice HRD as Companion Diagnostic for Niraparib," https://www.ajmo.com/view/myriad-genetics-submits-mychoice-hrd-as-companion-diagnostic-for-niraparib, (2019) pp. 1-3.

Gray, et al. "TumorNext: A comprehensive tumor profiling assay that incorporates high resolution copy number analysis and germline status to improve testing accuracy," www.impactjournals.com/oncotarget/, Oncotarget, vol. 7, No. 42, Published: Sep. 8, 2016, pp. 68206-68228.

Heeke, et al. "Prevalence of Homologous Recombination Deficiency (HRD) Among All Tumor Types," (2017), ASCO Annual Meeting '17, pp. 1-20.

A Phase I/II Study of MEDI4736 in Combination With Olaparib in Patients With Advanced Solid Tumors (MEDIOLA), U.S. National Library of Medicine, Last Update Posted: Mar. 2020, pp. 1-11.

A Study to Evaluate Rucaparib in Combination With Other Anti-cancer Agents in Patients With a Solid Tumor (SEASTAR), U.S. National Library of Medicine, Aug. 2019, pp. 1-6.

A Study of Durvalumab Alone and Durvalumab+Olaparib in Advanced, Platinum-Ineligible Bladder Cancer (BAYOU) (BAYOU), U.S. National Library of Medicine, Jan. 2020, pp. 1-8.

BeiGene Announces Clinical Data on Tislelizumab and Pamiparib Presented at the European Society for Medical Oncology (ESMO) Congress 2019, BeiGene, pp. 1-4 (Sep. 30, 2019).

DRAFT FoundationFocus CDxBRCA LOH Technical Information Summary, (2018), https://www.accessdata.fda.gov/cdrh_docs/pdf16/P160018S001C.pdf, pp. 1-27.

ESMO 2019: Pre-Specified Interim Analysis of GALAHAD: A Phase 2 Study of Niraparib in Patients with mCRPC and Biallelic DNA-Repair Gene Defects, (2019), pp. 1-3.

ESMO 2019: Preliminary Results from the TRITON2 Study of Rucaparib in Patients with DNA Damage Repair-deficient mCRPC: Updated Analyses, (2019), pp. 1-4.

FoundationFocus CDxBRCA LOH—P160018/S001C, pp. 1-2, (2018).

FoundationOne CDx—Technical Information, (2018), pp. 1-45.

FoundationOneLiquid FoundationOne Liquid is our next-generation liquid biopsy test for solid tumors utilizing circulating tumor DNA (ctDNA), (2020), pp. 1-5.

List of Cleared or Approved Companion Diagnostic Devices (In Vitro and Imaging Tools), (2019), pp. 1-7.

MyChoice CDx®—Technical Information, bit.ly/myChoiceCDxSpecs, 2019, pp. 1-17.

Tesaro's Niraparib Significantly Improved Progression-Free Survival, The Clearity Foundation, (2020), pp. 1-5.

Test Requisition Form, Foundation Medicine, pp. 1-2 (2018).

Test Request Form, MYRIAD myChoice CDx, pp. 1-2 (2019).

The Importance of HRD Testing, oncology,specialty pharmacy, HSE,hrd testing, (Nov. 27, 2019), pp. 1-2, https://www.pharmacytimes.com/view/the-importance-of-hrd-testing.

TumorNext-HRD, Ambry Genetics, pp. 1-3, 2020, https://web.archive.org/web/20200809111209/https://www.ambrygen.com/providers/genetic-testing/16/oncology/tumornext-hrd.

TumorNext-HRD: Paired Germline and Tumor Analyses of Genes Associated with Hereditary Ovarian Cancer, Sample Report, Ambry Genetics, 2018, pp. 1-7.

Tumor Test Requisition Form, Ambry Genetics, (2020), pp. 1-2.

What is Myriad myChoice CDx? MYRIAD myChoice CDx, (2020), https://bit.ly/myChoiceODxSpecs, pp. 1-5.

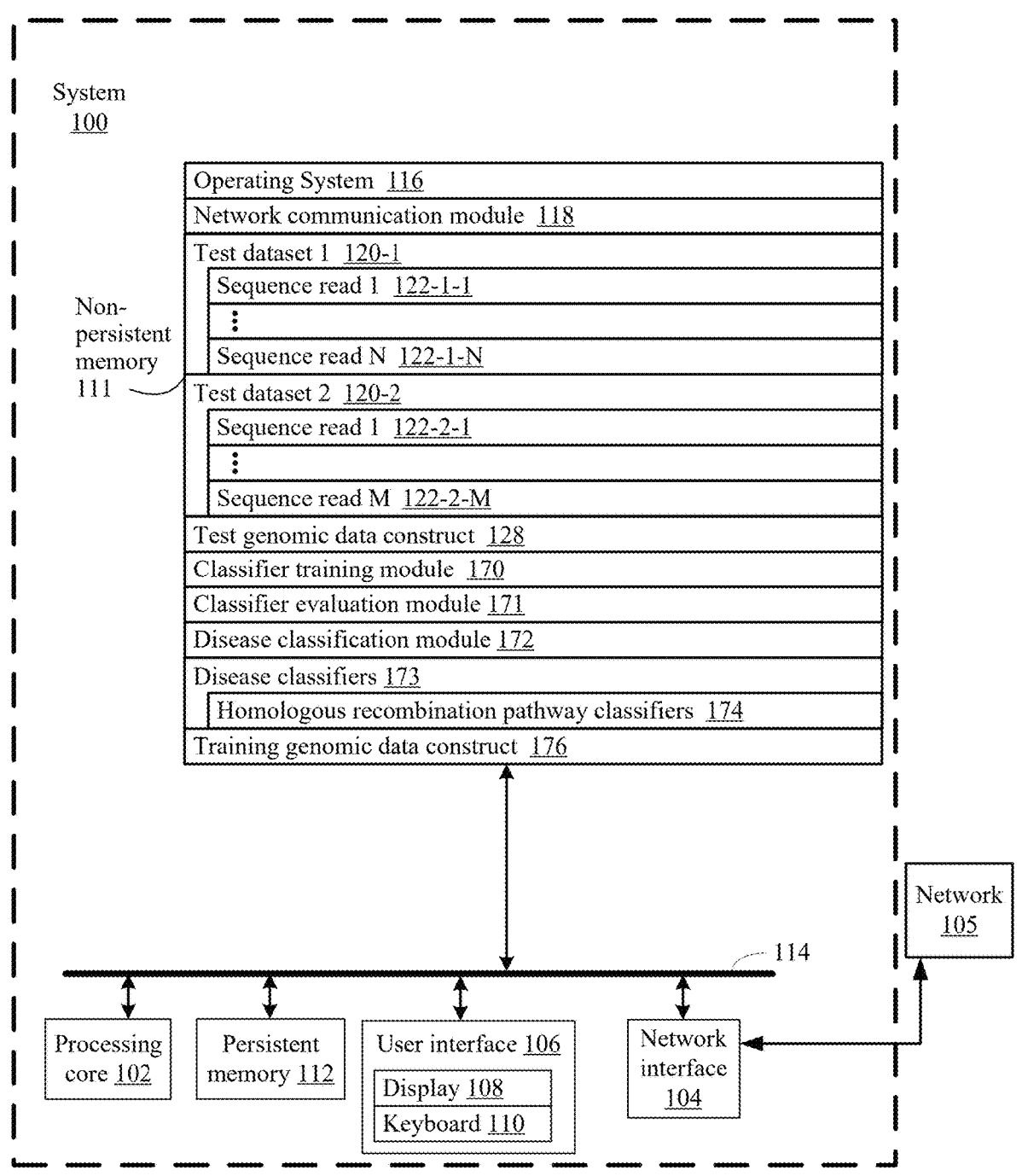

System
100

Non-persistent memory 111

| Operating System 116 |
| Network communication module 118 |

Test dataset 1 120-1
> Sequence read 1 122-1-1
> ⋮
> Sequence read N 122-1-N

Test dataset 2 120-2
> Sequence read 1 122-2-1
> ⋮
> Sequence read M 122-2-M

| Test genomic data construct 128 |
| Classifier training module 170 |
| Classifier evaluation module 171 |
| Disease classification module 172 |

Disease classifiers 173
> Homologous recombination pathway classifiers 174

| Training genomic data construct 176 |

114

Network
105

Processing core 102

Persistent memory 112

User interface 106
> Display 108
> Keyboard 110

Network interface 104

Fig. 1A

Figure 1B:
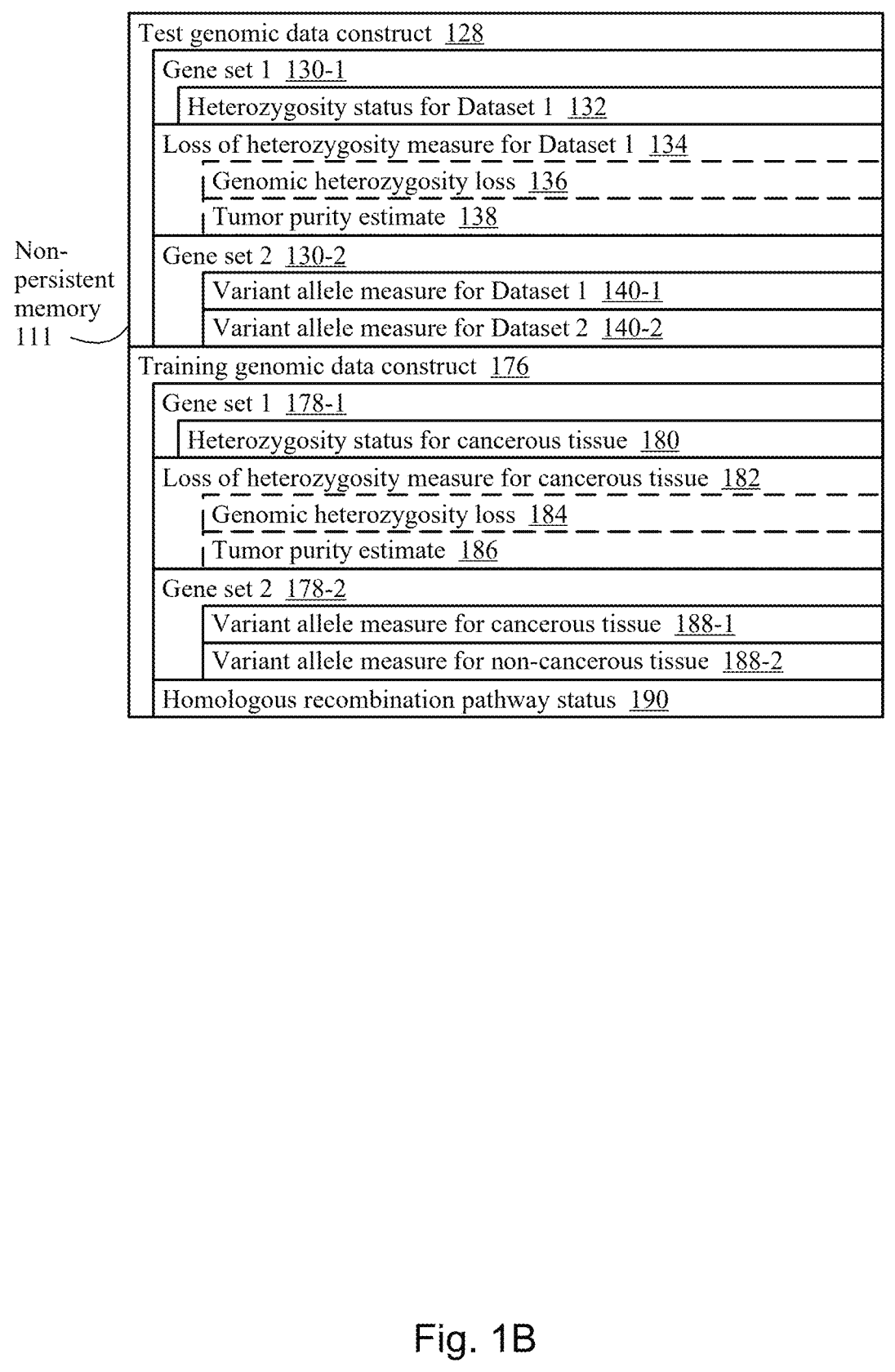

Non-persistent memory 111

Test genomic data construct 128

Gene set 1 130-1

Heterozygosity status for Dataset 1 132

Loss of heterozygosity measure for Dataset 1 134

Genomic heterozygosity loss 136

Tumor purity estimate 138

Gene set 2 130-2

Variant allele measure for Dataset 1 140-1

Variant allele measure for Dataset 2 140-2

Training genomic data construct 176

Gene set 1 178-1

Heterozygosity status for cancerous tissue 180

Loss of heterozygosity measure for cancerous tissue 182

Genomic heterozygosity loss 184

Tumor purity estimate 186

Gene set 2 178-2

Variant allele measure for cancerous tissue 188-1

Variant allele measure for non-cancerous tissue 188-2

Homologous recombination pathway status 190

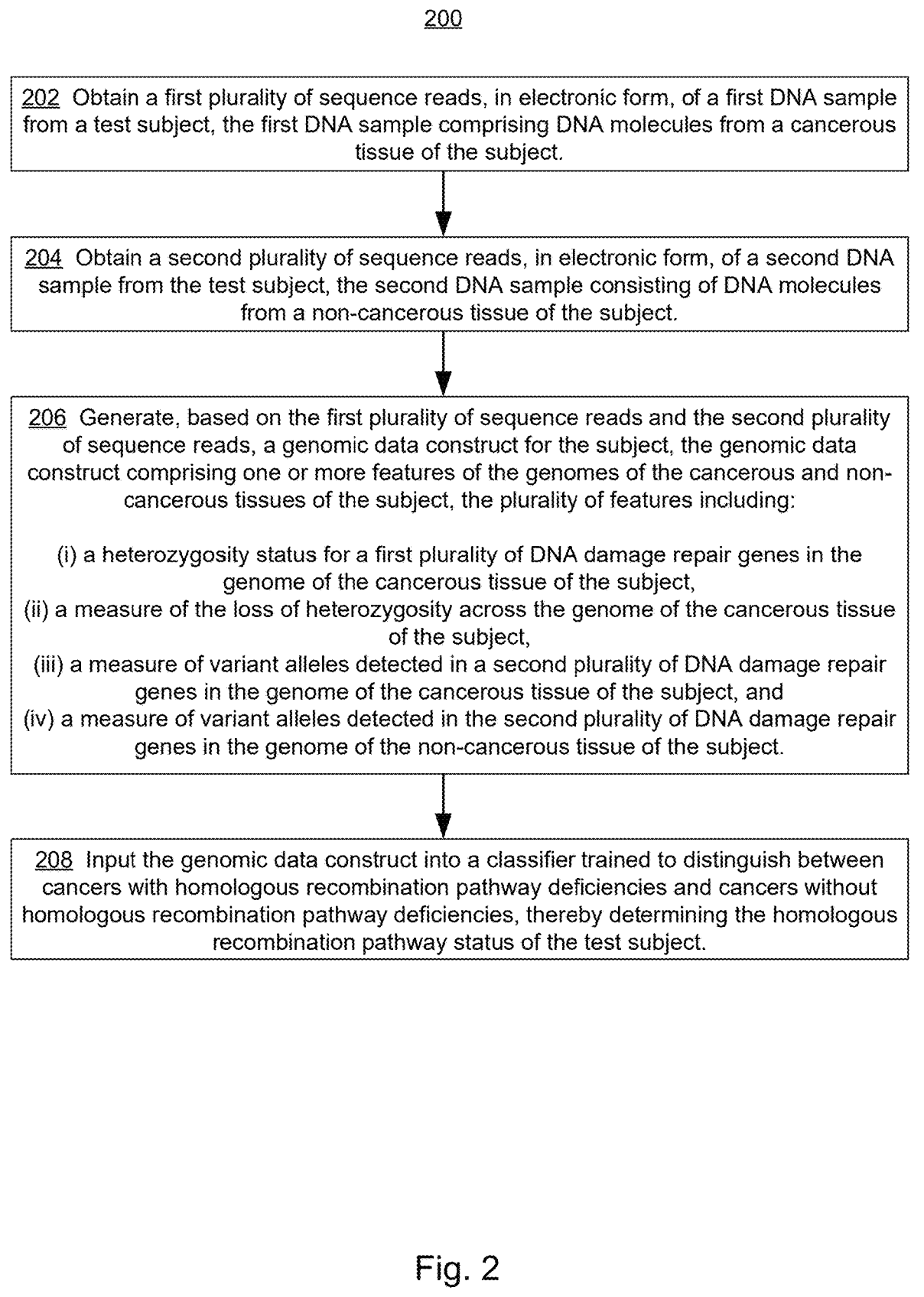

202 Obtain a first plurality of sequence reads, in electronic form, of a first DNA sample from a test subject, the first DNA sample comprising DNA molecules from a cancerous tissue of the subject.

204 Obtain a second plurality of sequence reads, in electronic form, of a second DNA sample from the test subject, the second DNA sample consisting of DNA molecules from a non-cancerous tissue of the subject.

206 Generate, based on the first plurality of sequence reads and the second plurality of sequence reads, a genomic data construct for the subject, the genomic data construct comprising one or more features of the genomes of the cancerous and non-cancerous tissues of the subject, the plurality of features including:

(i) a heterozygosity status for a first plurality of DNA damage repair genes in the genome of the cancerous tissue of the subject,
(ii) a measure of the loss of heterozygosity across the genome of the cancerous tissue of the subject,
(iii) a measure of variant alleles detected in a second plurality of DNA damage repair genes in the genome of the cancerous tissue of the subject, and
(iv) a measure of variant alleles detected in the second plurality of DNA damage repair genes in the genome of the non-cancerous tissue of the subject.

208 Input the genomic data construct into a classifier trained to distinguish between cancers with homologous recombination pathway deficiencies and cancers without homologous recombination pathway deficiencies, thereby determining the homologous recombination pathway status of the test subject.

Fig. 2

Figure 11:
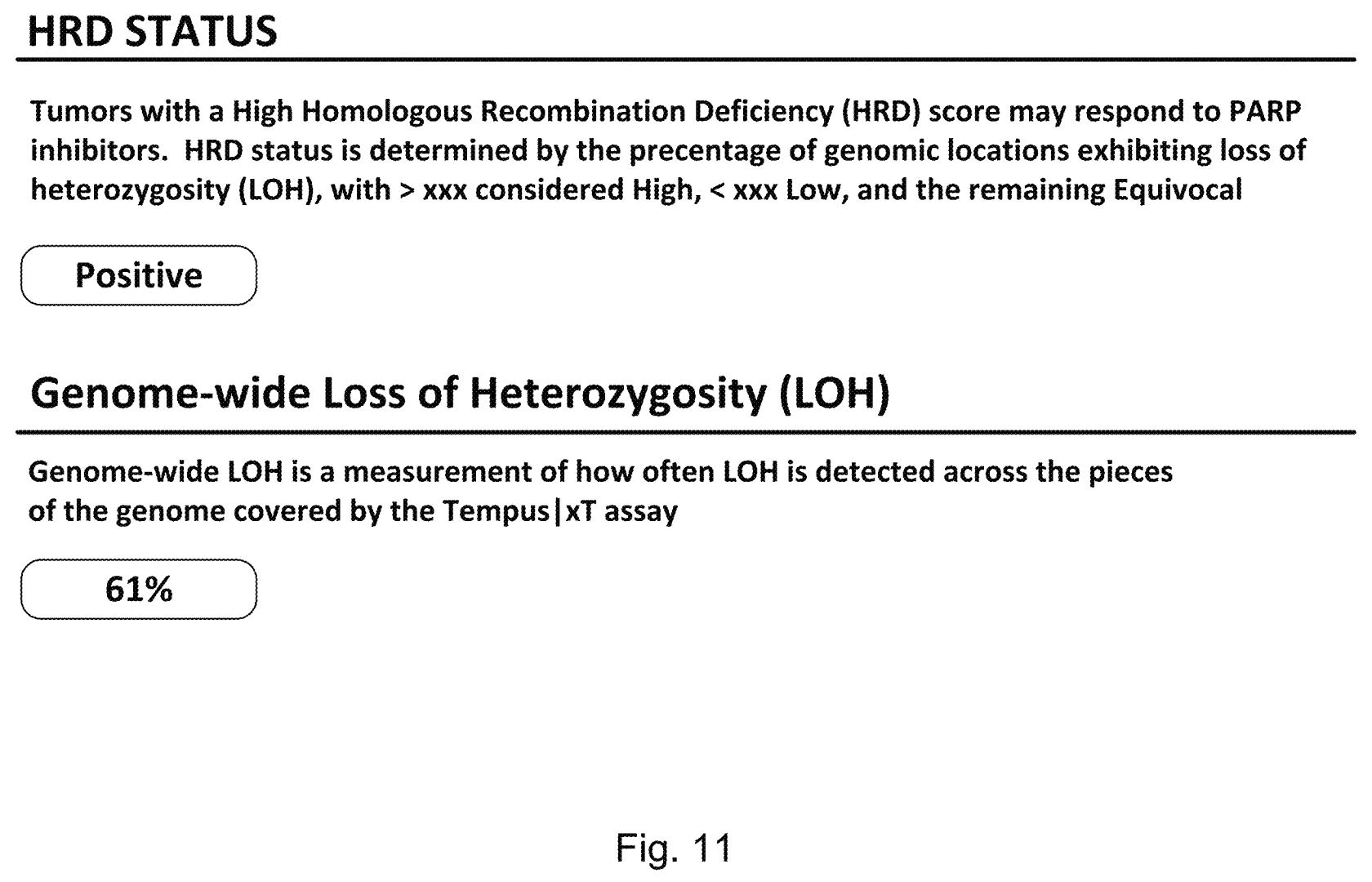

HRD STATUS

Tumors with a High High Homologous Recombination Deficiency (HRD) score may respond to PARP inhibitors. HRD status is determined by the precentage of genomic locations exhibiting loss of heterozygosity (LOH), with > xxx considered High, < xxx Low, and the remaining Equivocal Positive

Genome-wide Loss of Heterozygosity (LOH)

Genome-wide LOH is a measurement of how often LOH is detected across the pieces of the genome covered by the Tempus|xT assay

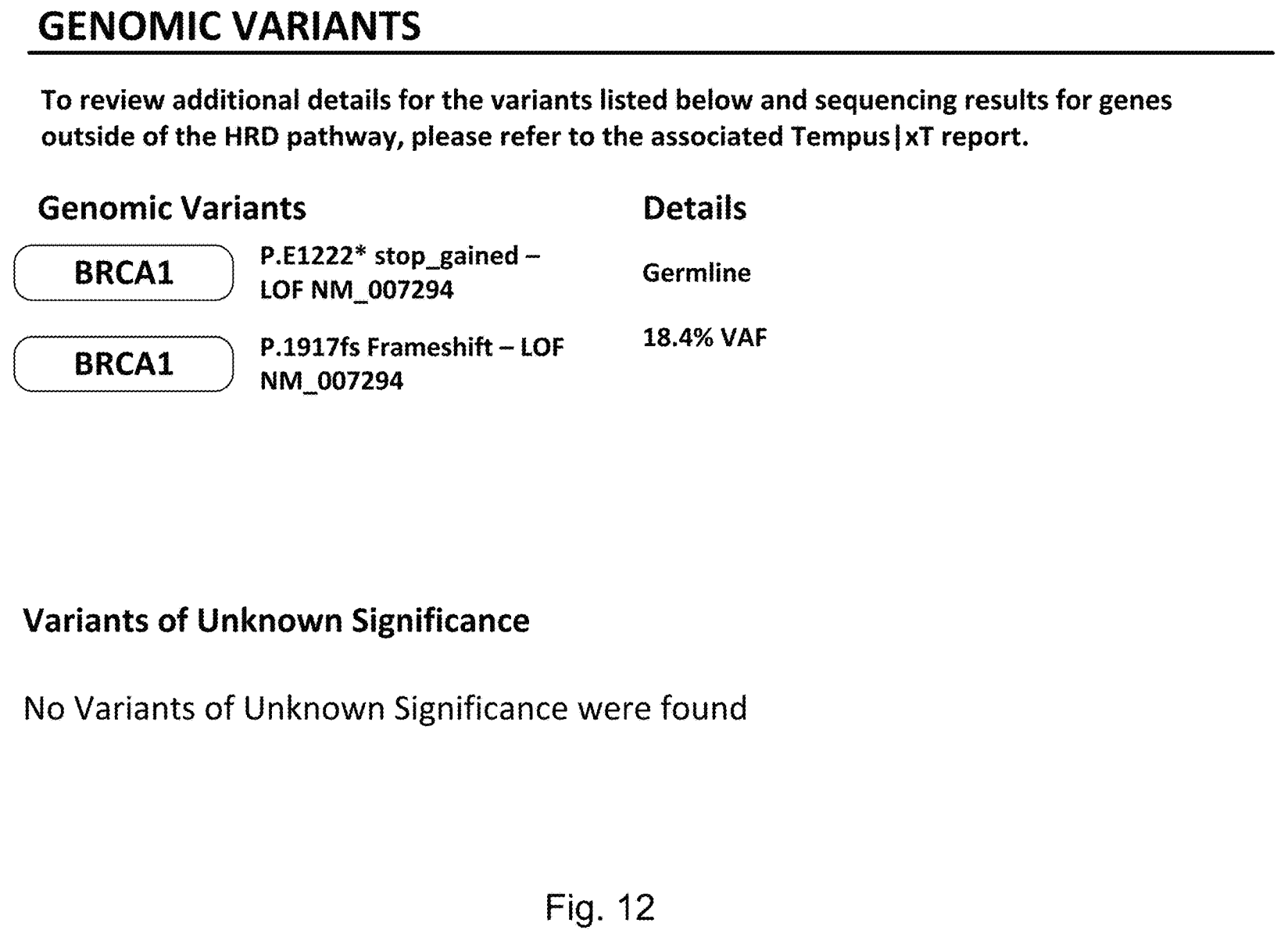

GENOMIC VARIANTS

To review additional details for the variants listed below and sequencing results for genes outside of the HRD pathway, please refer to the associated Tempus|xT report.

Genomic Variants                          Details

| BRCA1 | P.E1222* stop_gained –<br>LOF NM_007294 | Germline |
| BRCA1 | P.1917fs Frameshift – LOF<br>NM_007294 | 18.4% VAF |

Variants of Unknown Significance

No Variants of Unknown Significance were found

Fig. 12

INTEGRATED MACHINE-LEARNING FRAMEWORK TO ESTIMATE HOMOLOGOUS RECOMBINATION DEFICIENCY

CROSS REFERENCE TO RELATED APPLICATIONS

This application is a continuation application of U.S. patent application Ser. No. 16/789,363, filed Feb. 12, 2020, which claims priority to U.S. Provisional Patent Application No. 62/804,730, filed on Feb. 12, 2019, and U.S. Provisional Patent Application No. 62/946,347, filed on Dec. 10, 2019, the contents of which are hereby incorporated by reference in their entireties for all purposes.

TECHNICAL FIELD

The present disclosure relates generally to use of machine-learning classifiers trained against DNA sequencing of cancerous tissues to predict homologous recombination deficiency.

BACKGROUND

Precision oncology is the practice of tailoring cancer therapy to the unique genomic, epigenetic, and/or transcriptomic profile of an individual tumor. This is in contrast to conventional methods for treating a cancer patient based merely on the type of cancer the patient is afflicted with, e.g., treating all breast cancer patients with a first therapy and all lung cancer patients with a second therapy. Precision oncology was borne out of many observations that different patients diagnosed with the same type of cancer, e.g., breast cancer, responded very differently to common treatment regimes. Over time, researchers have identified genomic, epigenetic, and transcriptomic markers that facilitate some level of prediction as to how an individual cancer will respond to a particular treatment modality.

Therapy targeted to specific genomic alterations is already the standard of care in several tumor types (e.g., as suggested in the National Comprehensive Cancer Network (NCCN) guidelines for melanoma, colorectal cancer, and non-small cell lung cancer). These few, well known mutations in the NCCN guidelines can be addressed with individual assays or small next generation sequencing (NGS) panels. However, for the largest number of patients to benefit from personalized oncology, molecular alterations that can be targeted with off-label drug indications, combination therapy, or tissue agnostic immunotherapy should be assessed. See Schwaederle et al. 2016 *JAMA Oncol.* 2, 1452-1459; Schwaederle et al. 2015 *J Clin Oncol.* 32, 3817-3825; and Wheler et al. 2016 *Cancer Res.* 76, 3690-3701. Large panel NGS assays also cast a wider net for clinical trial enrollment. See Coyne et al. 2017 *Curr. Probl. Cancer* 41, 182-193; and Markman 2017 Oncology 31, 158,168.

Genomic analysis of tumors is rapidly becoming routine clinical practice to provide tailored patient treatments and improve outcomes. See Fernandes et al. 2017 *Clinics* 72, 588-594. Indeed, recent studies indicate that clinical care is guided by NGS assay results for 30-40% of patients receiving such testing. See Hirshfield et al. 2016 *Oncologist* 21, 1315-1325; Groisberg et al. 2017 *Oncotarget* 8, 39254-39267; Ross et al. *JAMA Oncol.* 1, 40-49; and Ross et al. 2015 *Arch. Pathol. Lab Med.* 139, 642-649. There is growing evidence that patients who receive therapeutic advice guided by genetics have better outcomes. See, for example Wheler et al. who used matching scores (e.g., scores based on the number of therapeutic associations and genomic aberrations per patient) to demonstrate that patients with higher matching scores have a greater frequency of stable disease, longer time to treatment failure, and greater overall survival (2016 *Cancer Res.* 76, 3690-3701). Such methods may be particularly useful for patients who have already failed multiple lines of therapy.

Targeted therapies have shown significant improvements in patient outcomes, especially in terms of progression-free survival. See Radovich et al. 2016 *Oncotarget* 7, 56491-56500. Recent evidence reported from the IMPACT trial, which involved genetic testing of advanced stage tumors from 3,743 patients and where approximately 19% of patients received matched targeted therapies based on their tumor biology, showed a response rate of 16.2% in patients with matched treatments versus 5.2% in patients with non-matched treatments. See Bankhead. "IMPACT Trial: Support for Targeted Cancer Tx Approaches." *MedPageToday*. Jun. 5, 2018. The IMPACT study further found that the three-year overall survival for patients given a molecularly matched therapy was more than twice that of non-matched patients (15% vs. 7%). See Id. and ASCO Post. "2018 ASCO: IMPACT Trial Matches Treatment to Genetic Changes in the Tumor to Improve Survival Across Multiple Cancer conditions." *The ASCO POST*. Jun. 6, 2018. Estimates of the proportion of patients for whom genetic testing changes the trajectory of their care vary widely, from approximately 10% to more than 50%. See Fernandes et al. 2017 *Clinics* 72, 588-594.

One example of a genomic trait that has been linked to the efficacy of particular therapies are mutations in the BRCA1, BRCA2, or PALB2 homologous recombination genes. A class of pharmacological inhibitors of Poly ADP ribose polymerase 1 (PARP1), known as PARP inhibitors (PARPi), have therapeutic efficacy for treating some cancers containing a mutation in the BRCA1, BRCA2, or PALB2 homologous recombination genes. PARP1 is an essential enzyme in the error-prone microhomology-mediated end joining (MMEJ) DNA repair pathway. Sharma S. et al., Cell Death Dis. 6 (3): e1697 (2015). In the absence of PARP1 activity, DNA replication forks stall when encountering a single-strand break. Fork stalling ultimately results in double-stranded chromosomal breaks that can be repaired by homologous recombination (HR) repair, which is much less error prone than the MMEJ pathway.

Unlike other DNA repair proteins, which are commonly deficient in cancer cells, PARP1 has been shown to be over-expressed in certain cancer types. It has been theorized that increased MMEJ DNA repair, relative to homologous repair, results in the accumulation of genomic mutations, which can lead to the development of cancer. However, the efficacy of PARP inhibitors is not completely understood. For instance, not all cancers with a BRCA1, BRCA2, or PALB2 mutation are sensitive to PARP inhibitors. Further, some cancers without a mutation in any homologous recombination protein are sensitive to PARP inhibitors.

Homologous recombination (HR) is a normal, highly conserved DNA repair process that enables the exchange of genetic information between identical or closely related DNA molecules. It is most widely used by cells to accurately repair harmful breaks (i.e. damage) that occur on both strands of DNA. DNA damage may occur from exogenous (external) sources like UV light, radiation, or chemical damage; or from endogenous (internal) sources like errors in DNA replication or other cellular processes that create DNA damage. Double strand breaks are a type of DNA damage.

Using poly (ADP-ribose) polymerase (PARP) inhibitors in patients with HRD compromises two pathways of DNA repair, resulting in cell death (apoptosis). The efficacy of PARP inhibitors is improved not only in ovarian cancers displaying germline or somatic BRCA mutations, but also in cancers in which HRD is caused by other underlying etiologies.

Poly (ADP-ribose) polymerase (PARP) is a family of proteins involved in a number of cellular processes such as DNA repair, genomic stability, and programmed cell death. Homologous recombination deficiency ("HR deficiency" or "HRD") is a deficiency that has been shown to increase the efficacy of PARP inhibitors (PARPi) and platinum-based therapies for patients. The most common lesions in cell DNA are single strand breaks (SSB), happening in tens of thousands per cells per day. PARPs are DNA repair enzymes that help repair single stranded breaks. When these PARPs are not working or are blocked (through a PARP inhibitor therapy, for example), this often leads to what are called double stranded breaks (DSBs). Homologous recombination repair (HRR) is the main way the body repairs these DSBs. If cancer cells have HRD (or, in other words, deficient HRR), the likelihood of the cell recovering from the DSB lowers, leading the cell into apoptosis (programmed cell death), instead of the cell continuing to proliferate. Causing cancer cells to die is one way to stop a person's cancer from growing.

HRD is considered by some as a disease state arising in tumors through loss of the homologous recombination DNA repair pathway, commonly caused by biallelic inactivation of BRCA1/2. The deficiency is often signaled by a mutation in the BRCA genes, but, as is common in cancer, there are other ways a tumor can have a HR deficiency.

Across cancers, HRD occurs at a frequency of about 6%. Rates can be as high as 30% for ovarian cancer, and intermediate for breast, pancreatic and prostate cancer (12-13%). HRD may be driven by biallelic inactivation of BRCA1, BRCA2, RAD51C and PALB2. Loss of heterozygosity (LOH) and deletions (especially of BRCA2) are also thought to be a major cause.

SUMMARY

Given the above background, what is needed in the art are improved ways to predict which cancers are homologous repair deficient (HRD), e.g., to identify which cancer patients are more likely to respond favorably to PARP inhibitors. The present disclosure addresses these and other needs by providing systems and methods for evaluating DNA sequencing results from cancerous tissues using a machine-learning algorithm trained to predict the homologous recombination status of a cancer.

Loss of homologous recombination is a widely-recognized determinant of cancer progression. Yet, few computational resources exist to estimate homologous recombination deficiency (HRD) from patient genomes. Genomics-based HRD testing is valuable for cancer diagnostics and could be used for patient stratification towards treatment with, for example, PARPi. Systems and methods are disclosed for the estimation of HRD status of a person's cancer.

In one aspect, the present disclosure provides a method for determining a homologous recombination pathway status of a cancer in a test subject. The method includes obtaining a first plurality of sequence reads, in electronic form, of a first DNA sample from the test subject, the first DNA sample including DNA molecules from a cancerous tissue of the subject. The method includes obtaining a second plurality of sequence reads, in electronic, of a second DNA sample from the test subject, the second DNA sample consisting of DNA molecules from a non-cancerous tissue of the subject. The method then includes generating, based on the first plurality of sequence reads and the second plurality of sequence reads, a genomic data construct for the subject, the genomic data construct comprising one or more a features of the genomes of the cancerous and non-cancerous tissues of the subject. In some embodiments, the plurality of features includes (i) a heterozygosity status for a first plurality of DNA damage repair genes in the genome of the cancerous tissue of the subject, (ii) a measure of the loss of heterozygosity across the genome of the cancerous tissue of the subject, (iii) a measure of variant alleles detected in a second plurality of DNA damage repair genes in the genome of the cancerous tissue of the subject, and (iv) a measure of variant alleles detected in the second plurality of DNA damage repair genes in the genome of the non-cancerous tissue of the subject. The method then includes inputting the genomic data construct into a classifier trained to distinguish between cancers with homologous recombination pathway deficiencies and cancers without homologous recombination pathway deficiencies, thereby determining the homologous recombination pathway status of the test subject.

In another aspect, the present disclosure provides a method for training an algorithm for determining a homologous recombination pathway status of a cancer. The method includes obtaining, for each respective training subject in a plurality of training subjects with cancer, a corresponding genomic data construct for the respective training subject. The corresponding genomic training construct includes (a) a homologous recombination pathway status for the cancer of the respective training subject and (b) one or more features of the genomes of cancerous and a non-cancerous tissues of the respective training subject. In some embodiments, the one or more features includes (i) a heterozygosity status for a first plurality of DNA damage repair genes in the genome of the cancerous tissue of the respective training subject, (ii) a measure of the loss of heterozygosity across the genome of the cancerous tissue of the respective training subject, (iii) a measure of variant alleles detected in a second plurality of DNA damage repair genes in the genome of the cancerous tissue of the respective training subject, and (iv) a measure of variant alleles detected in the second plurality of DNA damage repair genes in the genome of the non-cancerous tissue of the respective training subject. The method then includes training a classification algorithm against, for each respective training subject, at least (a) the homologous recombination pathway status for the cancer of the respective training subject, and (b) the plurality of features determined from the corresponding sample of DNA from the cancerous tissue of the respective training subject.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIGS. 1A and 1B collectively illustrates a block diagram of an example of a computing device for using information derived from DNA sequencing of cancerous tissue to predict the homologous recombination status of a cancer, in accordance with some embodiments of the present disclosure.

FIG. 2 provides a flow chart of an example method for using information derived from DNA sequencing of cancerous tissue to predict the homologous recombination status of a cancer, in accordance with some embodiments of the present disclosure.

FIG. 11 illustrates an example display of text and images that indicate HRD information, in accordance with some embodiments of the present disclosure.

FIG. 12 illustrates a portion of an example report listing genetic variants related to genes in the homologous recombination DNA repair pathway and/or genes that interact with this pathway, in accordance with some embodiments of the present disclosure.

Like reference numerals refer to corresponding parts throughout the several views of the drawings.

DETAILED DESCRIPTION

Figure 3:
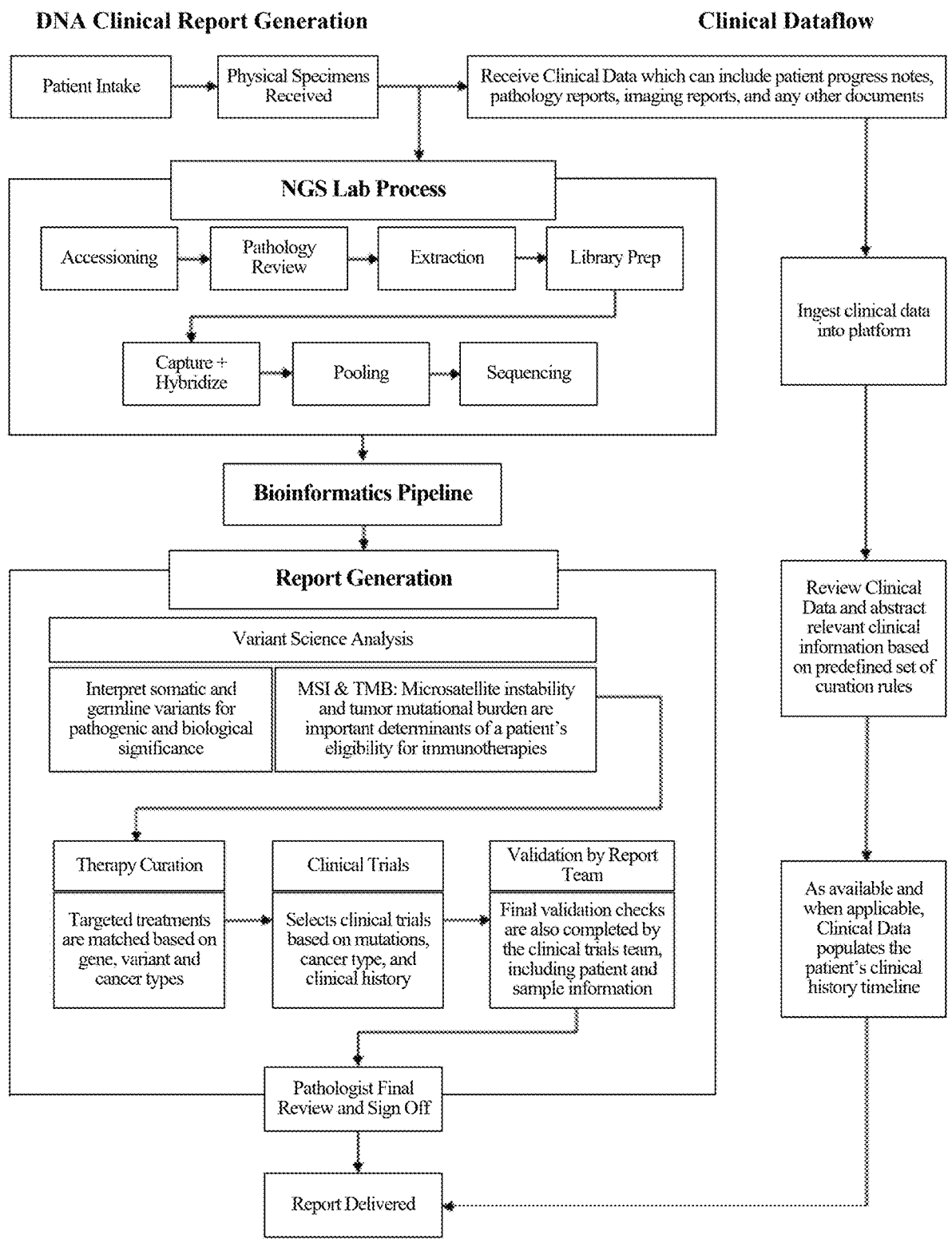
FIG. 3 illustrates an example of a method for generating a clinical report based off of information generated from analysis of one or more patient specimens.
Figure 4:
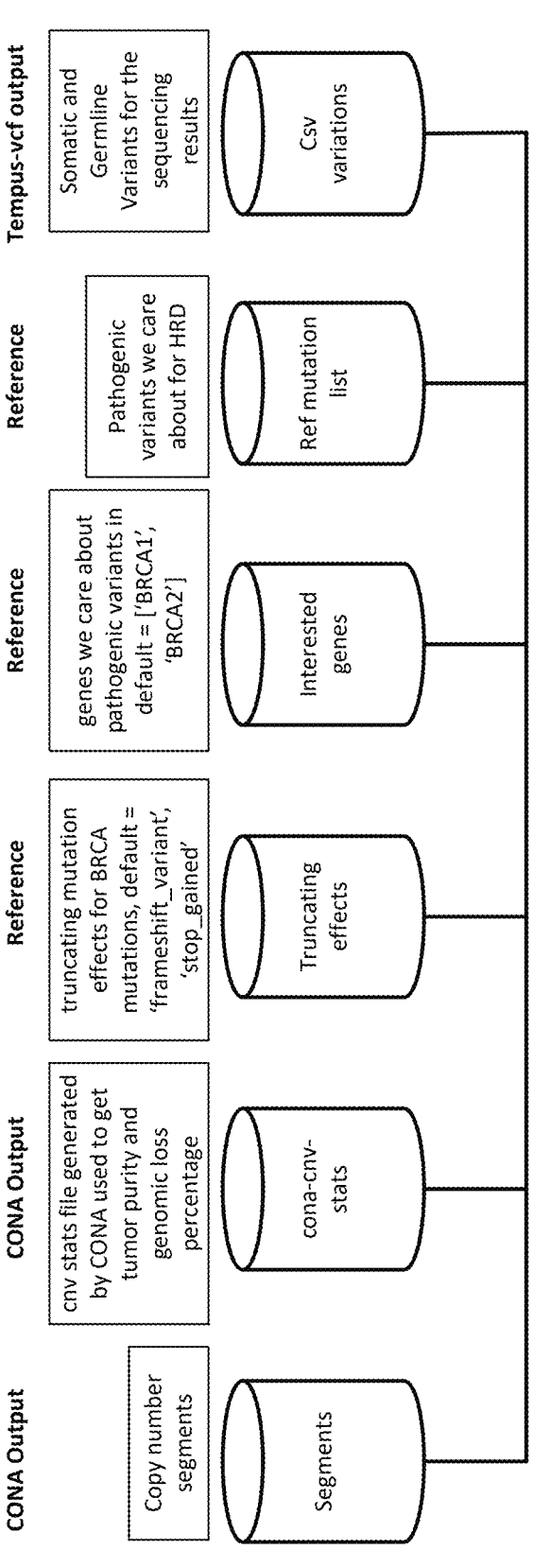
FIG. 4 illustrates example inputs for the HRD classification models, in accordance with some embodiments of the disclosure.

The present disclosure provides systems and methods for using information derived from DNA sequencing of cancerous tissue to predict the homologous recombination status of a cancer, to improve treatment predictions and outcomes. In some embodiments, sequencing data from matched cancerous tissue and germline tissue are used together to improve the accuracy of the predictions.

Definitions

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the term "subject" refers to any living or non-living human. In some embodiments, a subject is a male or female of any stage (e.g., a man, a women or a child).

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the term "locus" refers to a position (e.g., a site) within a genome, e.g., on a particular chromosome. In some embodiments, a locus refers to a single nucleotide position within a genome, i.e., on a particular chromosome. In some embodiments, a locus refers to a small group of nucleotide positions within a genome, e.g., as defined by a mutation (e.g., substitution, insertion, or deletion) of consecutive nucleotides within a cancer genome. Because normal mammalian cells have diploid genomes, a normal mammalian genome (e.g., a human genome) will generally have two copies of every locus in the genome, or at least two copies of every locus located on the autosomal chromosomes, e.g., one copy on the maternal autosomal chromosome and one copy on the paternal autosomal chromosome.

As used herein, the term "allele" refers to a particular sequence of one or more nucleotides at a chromosomal locus.

As used herein, the term "reference allele" refers to the sequence of one or more nucleotides at a chromosomal locus that is either the predominant allele represented at that chromosomal locus within the population of the species (e.g., the "wild-type" sequence), or an allele that is pre-defined within a reference genome for the species.

As used herein, the term "variant allele" refers to a sequence of one or more nucleotides at a chromosomal locus that is either not the predominant allele represented at that chromosomal locus within the population of the species (e.g., not the "wild-type" sequence), or not an allele that is predefined within a reference genome for the species.

As used herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the term "mutation" or "variant" refers to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein, the term "loss of heterozygosity" refers to the loss of one copy of a segment (e.g., including part or all of one or more genes) of the genome of a diploid subject (e.g., a human) or loss of one copy of a sequence encoding a functional gene product in the genome of the diploid subject, in a tissue, e.g., a cancerous tissue, of the subject. As used herein, when referring to a metric representing loss of heterozygosity across the entire genome of the subject, loss of heterozygosity is caused by the loss of one copy of various segments in the genome of the subject. Loss of heterozygosity across the entire genome may be estimated without sequencing the entire genome of a subject, and such methods for such estimations based on gene panel targeting-based sequencing methodologies are described in the art. Accordingly, in some embodiments, a metric representing loss of heterozygosity across the entire genome of a tissue of a subject is represented as a single value, e.g., a percentage or fraction of the genome. In some cases a tumor is composed of various sub-clonal populations, each of which may have a different degree of loss of heterozygosity across their respective genomes. Accordingly, in some embodiments, loss of heterozygosity across the entire genome of a cancerous tissue refers to an average loss of heterozygosity across a heterogeneous tumor population. As used herein, when referring to a metric for loss of heterozygosity in a particular gene, e.g., a DNA repair protein such as a protein involved in the homologous DNA recombination pathway (e.g., BRCA1 or BRCA2), loss of heterozygosity refers to complete or partial loss of one copy of the gene encoding the protein in the genome of the tissue and/or a mutation in one copy of the gene that prevents translation of a full-length gene product, e.g., a frameshift or truncating (creating a premature stop codon in the gene) mutation in the gene of interest. In some cases a tumor is composed of various sub-clonal populations, each of which may have a different mutational status in a gene of interest. Accordingly, in some embodiments, loss of heterozygosity for a particular gene of interest is represented by an average value for loss of heterozygosity for the gene across all sequenced sub-clonal populations of the cancerous tissue. In other embodiments, loss of heterozygosity for a particular gene of interest is represented by a count of the number of unique incidences of loss of heterozygosity in the gene of interest across all sequenced sub-clonal populations of the cancerous tissue (e.g., the number of unique frame-shift and/or truncating mutations in the gene identified in the sequencing data).

As used herein the term "cancer," "cancerous tissue," or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" refers to a biological sample obtained or derived from a tumor of a subject, as described herein.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as an mRNA transcript or a genomic locus.

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

As used herein, the term, "reference exome" refers to any particular known, sequenced or characterized exome, whether partial or complete, of any tissue from any organism or pathogen that may be used to reference identified sequences from a subject. Example reference exomes used for human subjects as well as many other organisms are provided in the on-line genome browser hosted by the National Center for Biotechnology Information ("NCBI").

As used herein, the term "reference genome" refers to any particular known, sequenced or characterized genome, whether partial or complete, of any organism or pathogen that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or pathogen, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

The term "classification" can refer to any number(s) or other characters(s) that are associated with a particular property of a sample. For example, in some embodiments, the term "classification" can refer to a type of cancer in a subject or sample, a stage of cancer in a subject or sample, a prognosis for a cancer in a subject or sample, a tumor load in a subject, a presence of tumor metastasis in a subject, and the like. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Example System Embodiments.

A detailed description of a system 100 for determining a homologous recombination pathway status of a cancer in a test subject and/or training an algorithm for determining a homologous recombination pathway status of a cancer is described in conjunction with FIGS. 1A-1B. As such, FIGS. 1A-1B collectively illustrate the topology of a system, in accordance with an embodiment of the present disclosure.

Referring to FIG. 1A, in typical embodiments, system 100 includes one or more computers. For purposes of illustration in FIG. 1A, system 100 is represented as a single computer that includes all of the functionality for identifying interactions within complex biological systems using data from a cell-based assay. However, in some embodiments, the functionality for determining the homologous recombination pathway status of a cancer in a test subject is spread across any number of networked computers and/or resides on each of several networked computers and/or is hosted on one or more virtual machines at a remote location accessible across the communications network 105. One of skill in the art will appreciate that any of a wide array of different computer topologies are used for the application and all such topologies are within the scope of the present disclosure.

Details of an example system are now described in conjunction with FIG. 1. FIG. 1 is a block diagram illustrating a system 100 in accordance with some implementations. Device 100 in some implementations includes at least one or more processing units CPU(s) 102 (also referred to as processors), one or more network interfaces 104, a user interface 106, e.g., including a display 108 and/or keyboard 110, a memory 111, and one or more communication buses 114 for interconnecting these components. The one or more communication buses 114 optionally include circuitry (sometimes called a chipset) that interconnects and controls communications between system components. The memory 111 may be a non-persistent memory, a persistent memory 112, or any combination thereof. The non-persistent memory typically includes high-speed random access memory, such as DRAM, SRAM, DDR RAM, ROM, EEPROM, flash memory, whereas the persistent memory typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. Regardless of its specific implementation, the memory 111 comprises at least one non-transitory computer readable storage medium, and it stores thereon computer-executable executable instructions which can be in the form of programs, modules, and data structures.

In some embodiments, as shown in FIG. 1A, the memory 111 stores:

an operating system 116, which includes procedures for handling various basic system services and for performing hardware-dependent tasks;

an optional network communication module (or instructions) 118 for connecting the system 100 with other devices and/or to a communication network 105;

a first test dataset 120-1 comprising a first plurality of sequence reads 122 (e.g., 122-1-1, . . . 122-1-N), in electronic form, of a first DNA sample from the test subject, the first DNA sample comprising DNA molecules from a cancerous tissue of the subject;

a second test dataset 120-2 comprising a second plurality of sequence reads 122 (e.g., 122-2-1, . . . , 122-2-M), in electronic form, of a second DNA sample from the test subject, the second DNA sample consisting of DNA molecules from a non-cancerous tissue of the subject;

a test genomic data construct 128 that is generated based on the first plurality of sequence reads and the second plurality of sequence reads, comprising one or more features of the genomes of the cancerous and non-cancerous tissues of the subject that can be inputted into a classifier trained to distinguish between cancers with homologous recombination pathway deficiencies and cancers without homologous recombination pathway deficiencies, comprising:

as illustrated in FIG. 1B, for a first plurality of DNA damage repair genes 130-1, a heterozygosity status in the genome of the cancerous tissue of the subject (e.g., the first dataset) 132;

a measure of the loss of heterozygosity across the genome of the cancerous tissue of the subject (e.g., the first dataset) 134, where the measure of the loss of heterozygosity across the genome of the cancerous tissue of the subject is optionally determined by determining a loss of genomic heterozygosity in the first plurality of sequence reads 136, and normalizing the determined loss of heterozygosity by an estimate of the tumor purity for the first plurality of sequence reads 138;

for a second plurality of DNA damage repair genes 130-2, a measure of variant alleles detected in the genome of the cancerous tissue of the subject (e.g., the first dataset) 140-1; and for the second plurality of DNA damage repair genes 130-2, a measure of variant alleles detected in the genome of the non-cancerous tissue of the subject (e.g., the second dataset) 140-2;

a classifier training module 170 for training disease classifiers 173 to distinguish between disease states, e.g., using training data stored in training genomic data construct 176;

disease classifiers 173, e.g., one or more homologous recombination pathway classifiers 174 for distinguishing between cancers with homologous recombination pathway deficiencies and cancers without homologous recombination pathway deficiencies;

a classifier evaluation module 171 for evaluating a disease classifier;

a disease classification module 172 for determining the homologous recombination pathway status of a test subject, e.g., by evaluating test genomic data construct 128 with a trained disease classifier 173; and a training genomic data construct 176 for a respective training subject, storing training genomic data that can be used to train an algorithm, e.g., disease classifiers 173, to determine a homologous recombination pathway status of a cancer, comprising a homologous recombination pathway status 190 for the cancer of the respective training subject and one or more features of the genomes of cancerous and non-cancerous tissues of the respective training subject, including:

as illustrated in FIG. 1B, for a first plurality of DNA damage repair genes 178-1, a heterozygosity status in the genome of the cancerous tissue of the subject 180;

a measure of the loss of heterozygosity across the genome of the cancerous tissue of the subject 182, where the measure of the loss of heterozygosity across the genome of the cancerous tissue of the subject is optionally determined by determining a loss of genomic heterozygosity in the first plurality of sequence reads 184, and normalizing the determined loss of heterozygosity by an estimate of the tumor purity for the first plurality of sequence reads 186;

for a second plurality of DNA damage repair genes 178-2, a measure of variant alleles detected in the genome of the cancerous tissue of the subject 188-1; and for the second plurality of DNA damage repair genes 178-2, a measure of variant alleles detected in the genome of the non-cancerous tissue of the subject 188-2.

In some implementations, modules 118, 170, 171 and/or 172 and/or data stores 120, 128 and/or 176 are accessible within any browser (e.g., installed on a phone, tablet, or laptop/desktop system). In some embodiments, modules 118, 120, 170, 171 and/or 172 run on native device frameworks, and are available for download onto the system 100 running an operating system 116, such as Windows, macOS, a Linux operating system, Android OS, or iOS.

In some implementations, one or more of the above identified data elements or modules of the system 100 are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 111 optionally stores a subset of the modules and data structures identified above. Furthermore, in some embodiments the memory 111 stores additional modules and data structures not described above. In some embodiments, one or more of the above-identified elements is stored in a computer system, other than that of system 100, that is addressable by system 100 so that system 100 may retrieve all or a portion of such data when needed.

Although FIG. 1 depicts a "system 100," the figure is intended as a functional description of the various features that may be present in computer systems than as a structural schematic of the implementations described herein. In practice, and as recognized by those of ordinary skill in the art, items shown separately could be combined and some items can be separate. Moreover, although FIG. 1 depicts certain data and modules in the memory 111 (which can be non-persistent 111 or persistent memory 112), it should be appreciated that these data and modules, or portion(s) thereof, may be stored in more than one memory.

Example Methods

Now that details of a system 100 for determining a homologous recombination pathway status of a cancer in a test subject and/or training an algorithm for determining a homologous recombination pathway status of a cancer have been disclosed, details regarding processes and features of the system, in accordance with various embodiment of the present disclosure, are disclosed below. Specifically, example processes are described below with reference to FIG. 2. In some embodiments, such processes and features of the system are carried out by modules 118, 120, 170, 171 and/or 172, as illustrated in FIG. 1. Referring to these methods, the systems described herein (e.g., system 100) include instructions for determining a homologous recombination pathway status of a cancer in a test subject and/or training an algorithm for determining a homologous recombination pathway status of a cancer.

FIG. 2 illustrates an example workflow 200 for determining a homologous recombination pathway status of a cancer in a test subject, in accordance with various embodiments of the present disclosure. Further details on various implementation of the steps illustrated in workflow 200 are described with more particularity below. The skilled artisan will know of suitable alternatives for performing each of the steps shown in workflow 200.

In one aspect, the disclosure provides a method 200 for determining a homologous recombination pathway status of a cancer in a test subject. The method includes obtaining (202) a first plurality of sequence reads, in electronic form, of a first DNA sample from the test subject, the first DNA sample including DNA molecules from a cancerous tissue of the subject. The method includes obtaining (204) a second plurality of sequence reads, in electronic, of a second DNA sample from the test subject, the second DNA sample consisting of DNA molecules from a non-cancerous tissue of the subject.

In some embodiments, the first DNA sample is from a solid tumor biopsy of the cancerous tissue of the subject. In other embodiments, the second DNA sample is from a liquid sample, e.g., a liquid biopsy. Generally, a cancerous biological sample of the subject is a biopsy. Methods for obtaining samples of cancerous tissue are known in the art, and are dependent upon the type of cancer being sampled. For example, bone marrow biopsies and isolation of circulating tumor cells can be used to obtain samples of blood cancers, endoscopic biopsies can be used to obtain samples of cancers of the digestive tract, bladder, and lungs, needle biopsies (e.g., fine-needle aspiration, core needle aspiration, vacuum-assisted biopsy, and image-guided biopsy, can be used to obtain samples of subdermal tumors, skin biopsies, e.g., shave biopsy, punch biopsy, incisional biopsy, and excisional biopsy, can be used to obtain samples of dermal cancers, and surgical biopsies can be used to obtain samples of cancers affecting internal organs of a patient. In some embodiments, the biological sample is a solid biopsy. In some embodiments, the solid biopsy is a macro-dissected formalin fixed paraffin embedded (FFPE) tissue section. In some embodiments, the biological sample comprises blood or saliva.

In some embodiments, the The first plurality of sequence reads was generated by targeted sequencing using a plurality of nucleic acid probes to enrich nucleic acids from the cancerous tissue of the subject for a panel of genomic regions. In some embodiments, the first plurality of sequence reads was generated by whole genome sequencing of nucleic acids from the cancerous tissue of the subject. In some embodiments, first plurality of sequence reads was generated by whole or partial exome sequencing of nucleic acids from the cancerous tissue of the subject.

In some embodiments, the second DNA sample is from a buffy coat preparation of a blood sample from the subject. In other embodiments, the second DNA sample is from saliva of the subject. Generally, any sample containing genomic or exomic material which is substantially all derived from non-cancerous tissues can be used to generate the second plurality of sequence reads.

In some embodiments, the second plurality of sequence reads was generated by targeted sequencing using a plurality of nucleic acid probes to enrich nucleic acids from the non-cancerous tissue of the subject for a panel of genomic regions. In some embodiments, the second plurality of sequence reads was generated by whole genome sequencing of nucleic acids from the non-cancerous tissue of the subject. In some embodiments, second plurality of sequence reads was generated by whole or partial exome sequencing of nucleic acids from the non-cancerous tissue of the subject.

The method then includes generating (206), based on the first plurality of sequence reads and the second plurality of sequence reads, a genomic data construct for the subject, the genomic data construct comprising one or more a features of the genomes of the cancerous and non-cancerous tissues of the subject. In some embodiments, the plurality of features includes (i) a heterozygosity status for a first plurality of DNA damage repair genes in the genome of the cancerous tissue of the subject, (ii) a measure of the loss of heterozygosity across the genome of the cancerous tissue of the subject, (iii) a measure of variant alleles detected in a second plurality of DNA damage repair genes in the genome of the cancerous tissue of the subject, and (iv) a measure of variant alleles detected in the second plurality of DNA damage repair genes in the genome of the non-cancerous tissue of the subject.

In some embodiments, the measure of the loss of heterozygosity across the genome of the cancerous tissue of the subject is obtained by determining a loss of genomic heterozygosity in the first plurality of sequence reads, and normalizing the determined loss of heterozygosity by an estimate of the tumor purity for the first plurality of sequence reads. That is, many 'tumor biopsies' contain a residual percentage of non-cancerous cells. When estimating the loss of heterozygosity from nucleic acids isolated from the tumor biopsy, the presence of nucleic acids from the non-cancerous cells will skew the overall loss of heterozygosity downwards. By estimating the tumor purity of the sample, e.g., the percentage of nucleic acids that are derived from cancerous cells rather than non-cancerous cells, the presence of non-cancerous contributions to the sequencing data can be accounted for, providing a more accurate estimate of the loss of heterozygosity across the cancer genome of the subject.

In some embodiments, the heterozygosity status for the first plurality of DNA damage repair genes comprises a count of the number of unique frameshift mutations detected in the first plurality of DNA damage repair genes. In some embodiments, the heterozygosity status for the first plurality of DNA damage repair genes comprises a count of the number of unique truncating mutations detected in the first plurality of DNA damage repair genes. In some embodiments, the first plurality of DNA damage repair genes are genes involved in the homologous recombination pathway. In some embodiments, the first plurality of DNA damage repair genes includes BRCA1 and BRCA2.

In some embodiments, the measure of variant alleles detected in the second plurality of DNA damage repair genes in the genome of the cancerous tissue of the subject includes a count of the number of unique mutations associated with loss of homologous recombination detected in the first plurality of sequence reads. In some embodiments, the measure of variant alleles detected in the second plurality of DNA damage repair genes in the genome of the non-cancerous tissue of the subject includes a count of the number of unique mutations associated with loss of homologous recombination detected in the second plurality of sequence reads.

In some embodiments, the second plurality of DNA damage repair genes are genes involved in the homologous recombination pathway. In some embodiments, the second plurality of DNA damage repair genes include BRCA1 and BRCA2. In some embodiments, the unique mutations associated with loss of homologous recombination in BRCA1 and BRCA2 include at least 25, 50, 75, 100, 125, or all of the mutations listed in Table 1.

The method then includes inputting (208) the genomic data construct into a classifier trained to distinguish between cancers with homologous recombination pathway deficiencies and cancers without homologous recombination pathway deficiencies, thereby determining the homologous recombination pathway status of the test subject. In some embodiments, the classifier is a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, or a clustering algorithm, as described in further detail below.

In some embodiments, method 200 also includes treating the subject based on the HRD prediction made by the classifier. For example, in some embodiments, when it is determined that the cancer in the test subject is homologous recombination deficient, treating the cancer by administering a poly ADP ribose polymerase (PARP) inhibitor to the test subject, and when it is determined the cancer in the test subject is not homologous recombination deficient, treating the cancer with a therapy that does not include administration of a PARP inhibitor to the test subject. In some embodiments, the PARP inhibitor is selected from olaparib, veliparib, rucaparib, niraparib, and talazoparib. A summary of current FDA approvals for various PARP inhibitors is provided in Table 2, below.

In another aspect, the present disclosure provides a method for training an algorithm for determining a homologous recombination pathway status of a cancer. The method includes obtaining, for each respective training subject in a plurality of training subjects with cancer, a corresponding genomic data construct for the respective training subject. The corresponding genomic training construct includes (a) a homologous recombination pathway status for the cancer of the respective training subject and (b) one or more features of the genomes of cancerous and a non-cancerous tissues of the respective training subject. In some embodiments, the one or more features includes (i) a heterozygosity status for a first plurality of DNA damage repair genes in the genome of the cancerous tissue of the respective training subject, (ii) a measure of the loss of heterozygosity across the genome of the cancerous tissue of the respective training subject, (iii) a measure of variant alleles detected in a second plurality of DNA damage repair genes in the genome of the cancerous tissue of the respective training subject, and (iv) a measure of variant alleles detected in the second plurality of DNA damage repair genes in the genome of the non-cancerous tissue of the respective training subject. The method then includes training a classification algorithm against, for each respective training subject, at least (a) the homologous recombination pathway status for the cancer of the respective training subject, and (b) the plurality of features determined from the corresponding sample of DNA from the cancerous tissue of the respective training subject.

FIG. 3 displays a flowchart of an exemplary method for generating a clinical report based off information generated from analysis of one or more patient specimens and ingestion of the patient's health information. A clinical laboratory may receive an order, such as an order for comprehensive genomic profiling or an order for a test that provides an estimate of HRD status. Physical specimens may be provided to a laboratory for processing and analysis. The processing and analysis may include analysis may nucleotide and clinical information that may include an estimate of HRD status. The one or more specimens may be processed through a laboratory, which may include the steps of accessioning, pathology review, extraction, library prep, capture and hybridization, pooling, and sequencing. Sequencing may be performed using next generation sequencing technologies, such as short-read technologies. Other sequencing methods, such as long-read sequencing or other sequencing methods known in the art, alternately may be used. Sequencing results may be provided to a bioinformatics pipeline. The results of the bioinformatics pipeline may be provided for variant science analysis, including the interpretation of variants (including somatic and germline variants as applicable) for pathogenic and biological significance. The variant science analysis may also estimate microsatellite instability (MSI) or tumor mutational burden. Targeted treatments may be identified based on gene, variant, and cancer type, for further consideration and review by the ordering physician. In some aspects, clinical trials may be identified for which the patient may be eligible, based on mutations, cancer type, and/or clinical history. A validation step may occur, after which the report may be finalized for signout and delivery. In some aspects, the report includes an estimate of HRD status. In other aspects, a second report may be delivered that has an estimate of HRD status, based on the information produced in parts of the method presented in FIG. 3.

Biological Samples

In some embodiments, the estimated HRD status may be generated based on information about the nucleotides of cancer and/or normal specimens. The cancer specimen may be from a cancer of different subtypes, including hematological and solid tumors. In some embodiments, the sample type utilized for comprehensive genomic profiling may be fixed formalin, paraffin embedded (FFPE) slides, peripheral blood, or bone marrow aspirate. The samples may be collected in a repository such a potassium ethylenediaminetetraacetic acid (EDTA) tube. The specimen may be a tissue block or a plurality of FFPE slides, such as up to 3 slides, up to 5 slides, up to 10 slides, or up to 20 slides. In some embodiments, the matched normal specimen is peripheral blood or saliva.

Features

In some aspects, the information used to produce an estimated HRD status may be produced by sequencing conducted by a multi-gene comprehensive genomic profiling panel. The panel may analyze more than 10, more than 100, or more than 1,000 genes. The panel may be a whole-exome panel that analyzes the exomes of a specimen. The panel may be a whole-genome panel that analyzes the genome of a specimen. In some aspects, the information used to produce an estimated HRD status may be produced as part of a comprehensive genomic profiling test, such as a DNA-based test. The panel may identify single nucleotide variations (SNVs), insertions/deletions, copy number variations (CNVs), and gene rearrangements.

The systems and methods may take into account the mutational status of certain genes. For example, the systems and methods may take into account mutational status of 1, 2, 3, 4, 5, 6, 7, 8, 9, 10, 11, 12, 13, 14, or 15 genes. The systems and methods may take into account mutational status of between 15-30 genes, between 30-45 genes, between 45-60 genes, between 60-75 genes, between 75-105 genes, and between 1-700 genes. The systems and methods may take into account commonly mutated genes in a pathway, such as the HR-pathway (Homologous Recombination Repair Mutations HRRm).

The systems and methods may employ a panel having a sensitivity of at least 99% for for base substitutions in at least 5% of mutant allele fraction; at least 98% for indels in at least 5% mutant allele fraction; at least 95% for CNVs from 8 or more gene copies in 30% or greater tumor nuclei, and/or at least 99% for gene arrangements, The panel may have an average sequencing depth of 500× for tumor. The panel may have an average sequencing depth of 150× for matched normal.

In some aspects, a report may be returned to a clinician with comprehensive genomic profiling information, such as information about the mutational status of a patient's cancer, as well as an estimate of HRD status. In some aspects, genes reported in the comprehensive genomic profiling information may be highlighted as underlying or otherwise related to the estimate of HRD status. The number of such genes may be between 1-5, between 1-10, between 1-20, between 1-30, between 1-40, between 1-50, and so forth. In some aspects, the genes reported as mutated in the comprehensive genomic profiling information may be highlighted as being germline or somatic alterations, where detected.

In some aspects, the systems and methods are scalable and may be utilized to permit integration with other genes in the DNA damage repair pathway, or other data-types such as RNA expression to provide clinical decision support with respect to treatment options, such as PARP inhibitor treatment options.

In the bioinformatics pipeline, various features may be generated that may be provided to an HRD prediction engine. In some embodiments, some or all of copy number segments, truncating and stop-gained effect pathogenic mutations in BRCA genes of interest, genome-wide LOH proportion, tumor purity and LOH in BRCA genes are used infer HRD status.

Tumor-normal matched sequencing analysis of patient specimens on a genetic sequencing panel and a subsequent bioinformatics pipeline may be used to call SNPs and copy number variants for each patient, which may be stored in a DNA variant data set.

Each DNA variant data set may be generated by processing a cancer sample and a non-cancer sample from the same patient through DNA whole exome next generation sequencing (NGS) to generate DNA sequencing data, and the DNA sequencing data may be processed by a bioinformatics pipeline to generate a DNA variant call file (among other outputs) for each sample. The cancer sample may be a tissue sample or blood sample containing cancer cells. In some instances, a tumor organoid sample may be processed instead of the patient cancer sample.

In more detail, germline ("normal", non-cancerous) DNA may be extracted from either blood (for example, if a patient has cancer that is not a blood cancer) or saliva (for example, if a patient has blood cancer). Normal blood samples may be collected from patients (for example, in PAXgene Blood DNA Tubes) and saliva samples may be collected from patients (for example, in Oragene DNA Saliva Kits).

Blood cancer samples may be collected from patients (for example, in EDTA collection tubes). Macrodissected FFPE tissue sections (which may be mounted on a histopathology slide) from solid tumor samples may be analyzed by pathologists to determine overall tumor amount in the sample and percent tumor cellularity as a ratio of tumor to normal nuclei. For each section, background tissue may be excluded or removed such that the section meets a tumor purity threshold (in one example, at least 20% of the nuclei in the section are tumor nuclei).

Then, DNA may be isolated from blood samples, saliva samples, and tissue sections using commercially available reagents, including proteinase K to generate a liquid solution of DNA.

Each solution of isolated DNA may be subjected to a quality control protocol to determine the concentration and/or quantity of the DNA molecules in the solution, which may include the use of a fluorescent dye and a fluorescence microplate reader, standard spectrofluorometer, or filter fluorometer.

For each cancer sample and each normal sample, isolated DNA molecules may be mechanically sheared to an average length using an ultrasonicator (for example, a Covaris ultrasonicator). The DNA molecules may also be analyzed to determine their fragment size, which may be done through gel electrophoresis techniques and may include the use of a device such as a LabChip GX Touch.

DNA libraries may be prepared from the isolated DNA, for example, using the KAPA Hyper Prep Kit, a New England Biolabs (NEB) kit, or a similar kit. DNA library preparation may include the ligation of adapters onto the DNA molecules. For example, UDI adapters, including Roche SeqCap dual end adapters, or UMI adapters (for example, full length or stubby Y adapters) may be ligated to the DNA molecules.

In this example, adapters are nucleic acid molecules that may serve as barcodes to identify DNA molecules according to the sample from which they were derived and/or to facilitate the downstream bioinformatics processing and/or the next generation sequencing reaction. The sequence of nucleotides in the adapters may be specific to a sample in order to distinguish samples. The adapters may facilitate the binding of the DNA molecules to anchor oligonucleotide molecules on the sequencer flow cell and may serve as a seed for the sequencing process by providing a starting point for the sequencing reaction.

DNA libraries may be amplified and purified using reagents, for example, Axygen MAG PCR clean up beads. Then the concentration and/or quantity of the DNA molecules may be quantified using a fluorescent dye and a fluorescence microplate reader, standard spectrofluorometer, or filter fluorometer.

DNA libraries may be pooled (two or more DNA libraries may be mixed to create a pool) and treated with reagents to reduce off-target capture, for example Human COT-1 and/or IDT xGen Universal Blockers. Pools may be dried in a vacufuge and resuspended. DNA libraries or pools may be hybridized to a probe set (for example, a probe set specific to a panel that includes approximately 100, 600, 1,000, 10,000, etc. of the 19,000 known human genes) and amplified with commercially available reagents (for example, the KAPA HiFi HotStart ReadyMix).

Pools may be incubated in an incubator, PCR machine, water bath, or other temperature modulating device to allow probes to hybridize. Pools may then be mixed with Streptavidin-coated beads or another means for capturing hybridized DNA-probe molecules, such as DNA molecules representing exons of the human genome and/or genes selected for a genetic panel.

Pools may be amplified and purified more than once using commercially available reagents, for example, the KAPA HiFi Library Amplification kit and Axygen MAG PCR clean up beads, respectively. The pools or DNA libraries may be analyzed to determine the concentration or quantity of DNA molecules, for example by using a fluorescent dye (for example, PicoGreen pool quantification) and a fluorescence microplate reader, standard spectrofluorometer, or filter fluorometer.

In one example, the DNA library preparation and/or whole exome capture steps may be performed with an automated system, using a liquid handling robot (for example, a SciClone NGSx).

The library amplification may be performed on a device, for example, an Illumina C-Bot2, and the resulting flow cell containing amplified target-captured DNA libraries may be sequenced on a next generation sequencer, for example, an Illumina HiSeq 4000 or an Illumina NovaSeq 6000 to a unique on-target depth selected by the user, for example, 300×, 400×, 500×, 10,000×, etc. Samples may be further assessed for uniformity with each sample required to have 95% of all targeted bp sequenced to a minimum depth selected by the user, for example, 300×. The next generation sequencer may generate a FASTQ, BCL, or other file for each flow cell or each patient sample.

Bioinformatics Pipeline

Figure 5:
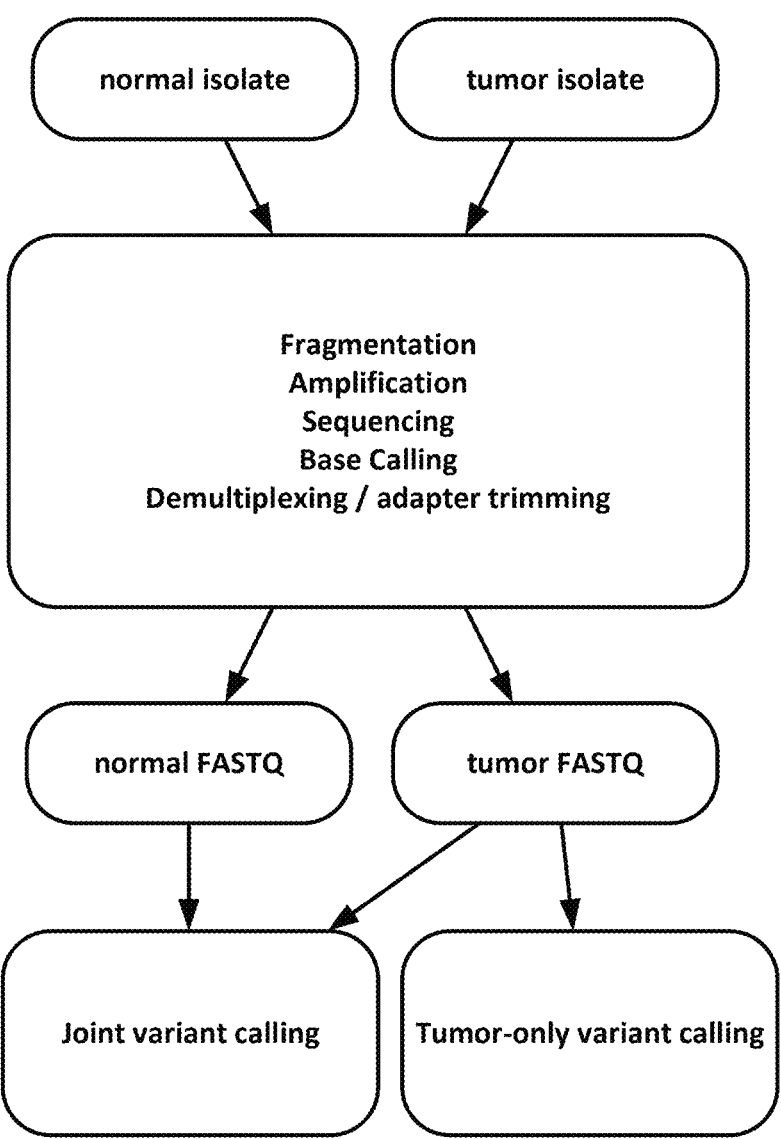
FIG. 5 illustrates an example bioinformatics pipeline for tumor-normal matched variant calling and tumor-only calling, in accordance with some embodiments of the present disclosure.

In certain aspects, the bioinformatics pipeline includes the systems and methods disclosed in this document FASTQ and Alignment When a matched normal tissue is available for a patient, a tumor-normal matched sequencing run is performed. DNA is extracted from the normal tissue, typically blood or saliva. This is then sequenced in addition to the DNA extracted from the tumor tissue. These two sequencing runs, one for the tumor tissue, and one for the normal tissue, produce two FASTQ output files. FASTQ format is a text-based format for storing both a biological sequence, such as nucleotide sequence, and its corresponding quality scores. These FASTQ files are analyzed to determine what genetic variants or copy number changes are present in the sample. A 'matched' panel-specific workflow is run to jointly analyze the tumor-normal matched FASTQ files. When a matched normal is not available, FASTQ files from the tumor tissue are analyzed in the 'tumor-only' mode. See, for example, FIG. 5.

If two or more patient samples are processed simultaneously on the same sequencer flow cell, a difference in the sequence of the adapters used for each patient sample could serve the purpose of a barcode to facilitate associating each read with the correct patient sample and placing it in the correct FASTQ file.

Figure 6:
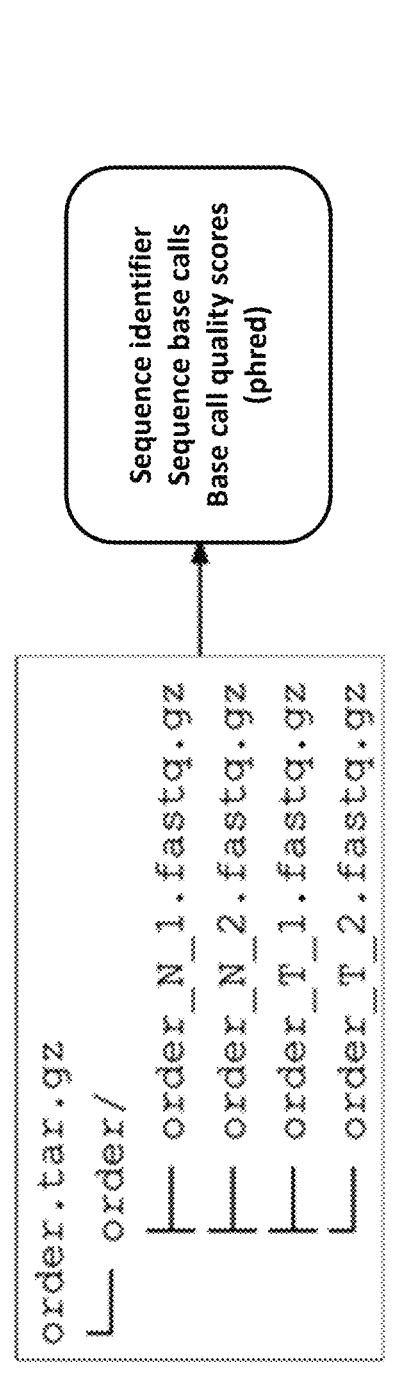
FIG. 6 illustrates that paired-end reads from tumor and normal isolates are zipped and stored separately under the same order identifier, in accordance with some embodiments of the present disclosure.

For efficiency, the results of paired-end sequencing of each isolate are contained in a split pair of FASTQ files. Forward (Read 1) and reverse (Read 2) sequences of each tumor and normal isolate are stored separately but in the same order and under the same identifier. See, for example, FIG. 6.

Figure 7:
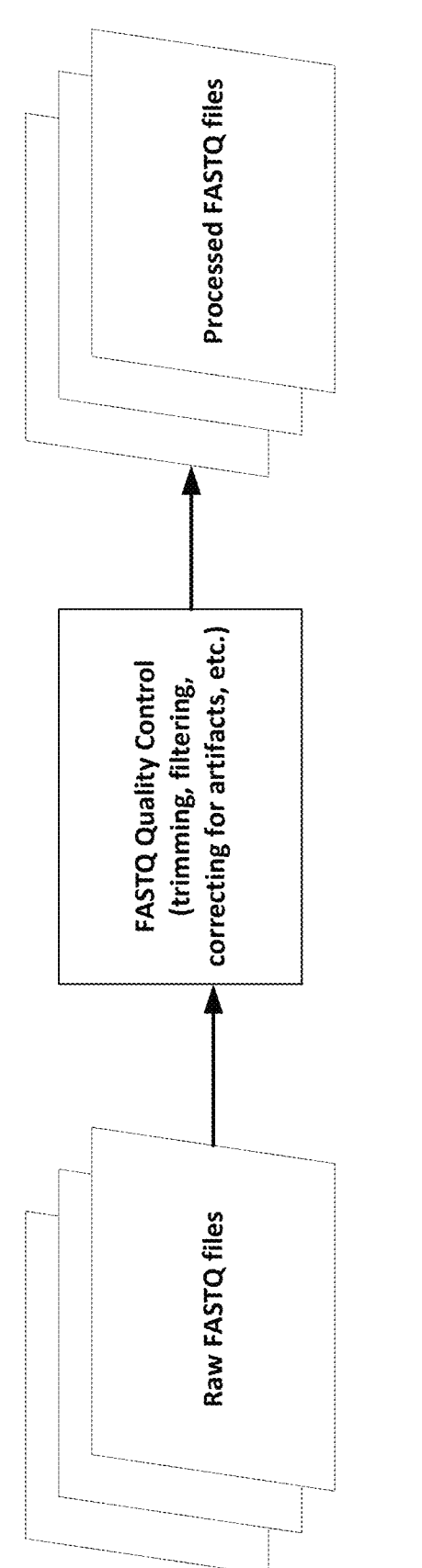
FIG. 7 illustrates quality correction for FASTQ files, in accordance with some embodiments of the present disclosure.

In various embodiments, the bioinformatics pipeline may filter FASTQ data from each isolate. Such filtering may include correcting or masking sequencer errors and removing (trimming) low quality sequences or bases, adapter sequences, contaminations, chimeric reads, overrepresented sequences, biases caused by library preparation, amplification, or capture, and other errors (FIG. 7). Entire reads, individual nucleotides, or multiple nucleotides that are likely to have errors may be discarded based on the quality rating associated with the read in the FASTQ file, the known error rate of the sequencer, and/or a comparison between each nucleotide in the read and one or more nucleotides in other reads that has been aligned to the same location in the reference genome. Filtering may be done in part or in its entirety by various software tools, for example, a software tool such as Skewer (see internet address doi.org/10.1186/1471-2105-15-182). FASTQ files may be analyzed for rapid assessment of quality control and reads, for example, by a sequencing data QC software such as AfterQC, Kraken, RNA-SeQC, FastQC, (see Illumina, BaseSpace Labs or internet address illumina.com/products/by-type/informatics-products/basespace-sequence-hub/apps/fastqc.html), or another similar software program. For paired-end reads, reads may be merged.

In a matched panel-specific tumor-normal analysis, each FASTQ file, one for tumor, and one from normal (if available) are analyzed. In the tumor-only analysis, only tumor FASTQ is available for analysis.

Figure 8:
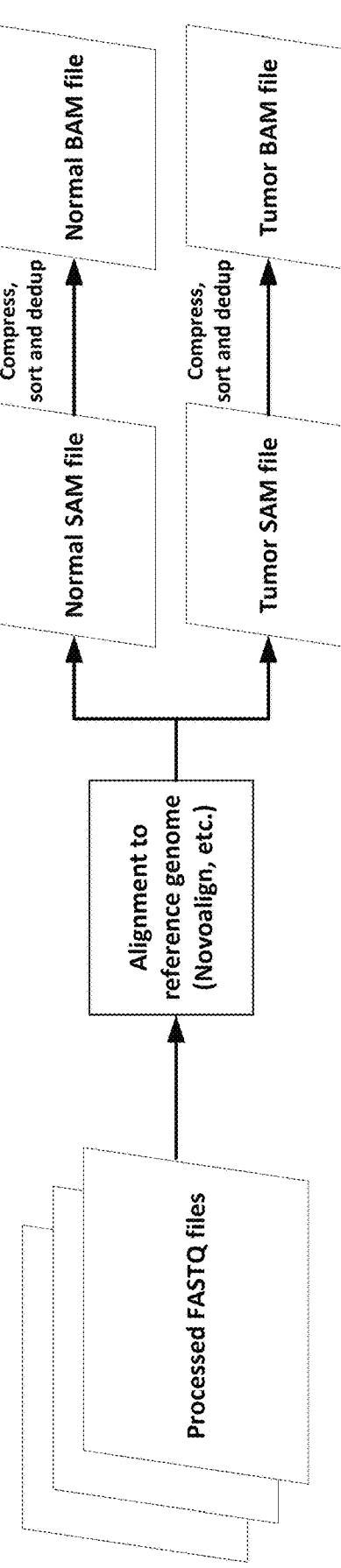
FIG. 8 illustrates steps for obtaining tumor and normal BAM alignment files, in accordance with some embodiments of the present disclosure.

Each read from the FASTQ(s) may be aligned to a location in the human genome having a sequence that best matches the sequence of nucleotides in the read. There are many software programs designed to align reads, for example, Novoalign (Novocraft, Inc.), Bowtie, Burrows Wheeler Aligner (BWA), programs that use a Smith-Waterman algorithm, etc. Alignment may be directed using a reference genome (for example, hg19, GRCh38, hg38, GRCh37, other reference genomes developed by the Genome Reference Consortium, etc.) by comparing the nucleotide sequences in each read with portions of the nucleotide sequence in the reference genome to determine the portion of the reference genome sequence that is most likely to correspond to the sequence in the read. The alignment may generate a SAM file, which stores the locations of the start and end of each read according to coordinates in the reference genome and the coverage (number of reads) for each nucleotide in the reference genome. The SAM files may be converted to BAM files, BAM files may be sorted, and duplicate reads may be marked for deletion, resulting in de-duplicated BAM files. This process produces a tumor BAM file, and a normal BAM file (when available) (e.g., as illustrated in FIG. 8). In various embodiments, BAM files may be analyzed to detect genetic variants and other genetic features, including single nucleotide variants (SNVs), copy number variants (CNVs), gene rearrangements, etc. In various aspects, the detected genetic variants and genetic features may be analyzed as a form of quality control. For example, a pattern of detected genetic variants or features may indicate an issue related to the sample, sequencing procedure, and/or bioinformatics pipeline, for example, contamination of the sample, mislabeling of the sample, a change in reagents, a change in the sequencing procedure and/or bioinformatics pipeline, etc.

Calling SNVs and Indels

Figure 9:
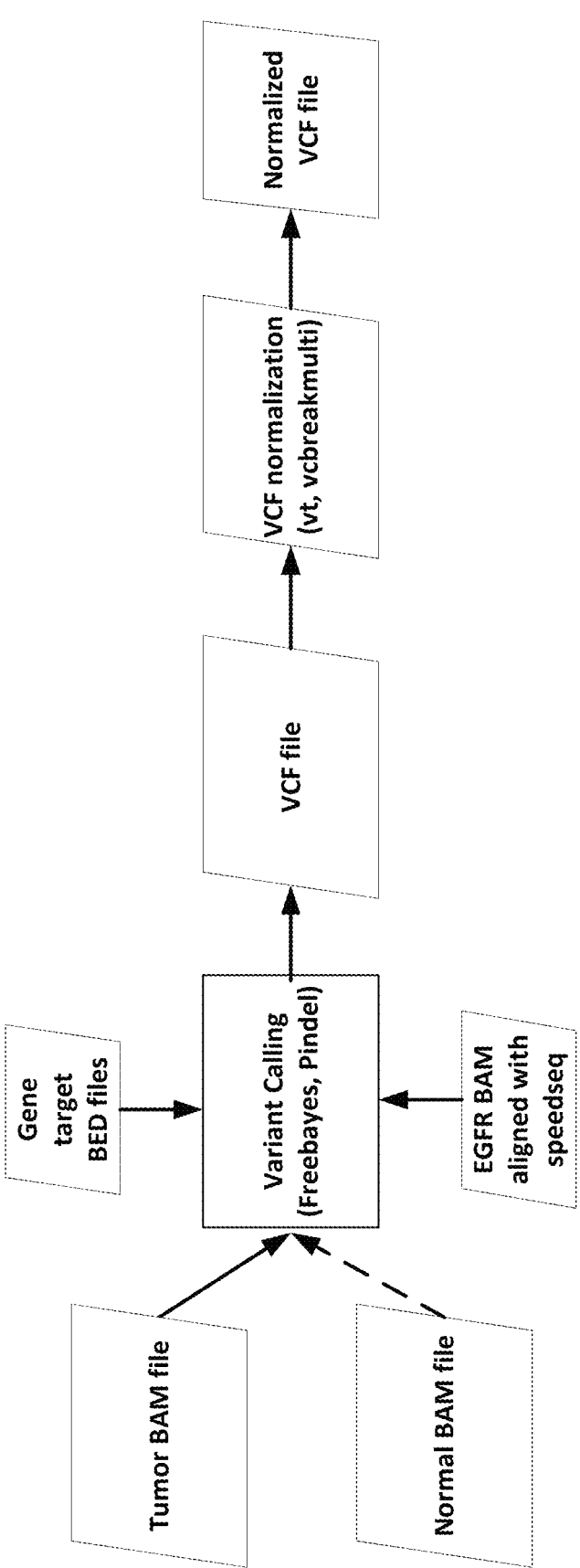
FIG. 9 illustrates steps for calling variants from tumor and normal BAM alignment files, in accordance with some embodiments of the present disclosure.

Following alignment, tools like SamBAMBA may be used for marking and filtering duplicates on the sorted bams. Software packages such as freebayes and pindel are used to call variants using the sorted BAM files as the input, together with genome and panel bed files containing the gene targets to analyze as the reference. A raw VCF file (variant call format) file is output, showing the locations where the nucleotide base in the sample is not the same as the nucleotide base in that position in the reference genome. Software packages such as vcfbreakmulti and vt are used to normalize multi-nucleotide polymorphic variants in the raw VCF file and a variant normalized VCF file is output. SNVs in the VCFs are annotated using SNPEff for transcript information, mutation effects and prevalence in 1000 genomes databases. EGFR variants are called separately through re-alignment of tumor and normal fastq files on chr 7 using speedseq. Duplicates are marked using tools such as Sambamba, and variant calling is done analogous to the steps described for other chromosomes. See, for example, FIG. 9.

Determining Copy Number Variant

In various embodiments, the systems and methods include copy number analysis methods to compute the genomic features used to estimate HRD status. For example, in some embodiments, to assess copy number, de-duplicated BAM files and a VCF generated from the variant calling pipeline may be used to compute read depth and variation in heterozygous germline SNVs between the tumor and normal samples. If a matched normal sample is not available, comparison between a tumor sample and a pool of process matched normal controls may be utilized. Circular binary segmentation may be applied and segments may be selected with highly differential log 2 ratios between the tumor and its comparator (matched normal or normal pool). Approximate integer copy number may be assessed from a combination of differential coverage in segmented regions and an estimate of stromal admixture (for example, tumor purity, or the portion of a sample that is tumor vs. non-tumor) generated by analysis of heterozygous germline SNVs.

Determining Loss of Heterozygosity

In some aspects, LOH may be determined through the use of a copy number calling algorithm. First, the tumor purity and copy states in the tumor genome may be estimated using an expectation maximization algorithm (EM). Estimation of copy states and tumor purity may involve the following steps: 1) Read alignment and normalization 2) Computation of B-allele frequencies and deviations 3) Preliminary estimation of tumor purity 4) Genomic segmentation, and 5) Refinement of initial tumor purity estimate and estimation of copy states and LOH via EM algorithm.

Read alignment and normalization. To compute probe target coverage, sequenced reads from the tumor may be aligned to the human reference genome and normalized by length and depth and GC content. Reads from the normal tissue may also be processed similarly, when available. If a matched normal is not available, a normal pool, consisting of read coverages from normal healthy individuals not known to have cancer may be used. To select a gender-matched normal pool, a gender estimation step may be performed by mapping the variants to the X-chromosome together with the X-chromosome coverages. From the normal pool, the closest neighbours may be chosen, for instance through the application of a PCA selection step. Their coverage values may be used to normalize tumor coverages. This PCA selection increases the sensitivity of somatic CNV detection. Finally, the read coverage may be expressed as the ratio of tumor coverage to normal coverage and log 2 transformed.

Computation of B-allele frequencies and deviations. Heterozygous variants contain useful information about copy numbers and LOH. These variants may be mined from the somatic and germline variant calls made using freebayes and pindel. B-allele frequency (BAF) deviations from the expected normal values are calculated for each heterozygous SNP, and also represented as the BAF log-odds ratio. If a variant is normal germline, the BAF deviation from normal should be close to 0. For a variant that shows LOH, BAF deviates significantly from 0.

Preliminary estimation of tumor purity. Initial estimations for tumor purity may be obtained from somatic variants and BAF data, to be used as input for the EM algorithm. The maximum VAF of a somatic variant should in theory equal the tumor purity. This is the somatic estimate of tumor purity. From the BAF data, for a variant that shows log odds-ratio greater than 2 is clearly LOH, as such significant deviations are only expected when a copy is lost, or copy-neutral. Twice the maximum possible VAF for such a variant should in theory equal the tumor purity, and corresponds to the BAF estimate. These two estimates are averaged to form the initial estimate of tumor purity.

Genomic segmentation. A bi-variate segmentation of the genome is performed using tumor to normal coverage ratios and BAF log-odds data. A series of rolling T-tests are performed across the genome using an algorithm similar to circular binary segmentation to identify the sections of the genome where a significant switch in copy numbers is observed. This collapses the whole genome into segments, each of which has a distinct copy number profile. The segmentation branching and pruning threshold parameters control how much segmentation and focal segment detection is possible, and is optimized for Tempus data.

Refinement of initial tumor purity estimate and estimation of copy states and LOH via EM algorithm. From the initial guesses of tumor purity, a range of tumor purity values, from half the tumor purity to maximum possible value are iterated over to estimate the best fit copy states for each genomic segment. For each tumor purity estimate and genomic segment, the expected log-ratio and BAF is computed for each copy state ranging from 0 to 20, only allowing for meaningful copy state combinations. The likelihood of observed coverage and BAF is then calculated given these expectations from the bivariate probability density function and a likelihood matrix is constructed. The copy state with the maximum likelihood is returned from this matrix. This process is iterated over all segments, and a segment to best-fit copy state map is constructed. Repeating this step for all tumor purities generates a tumor-purity likelihood matrix, and the tumor purity with smallest model error and the maximum likelihood is returned as the final estimate. Once the copy state assignments are available for all genomic segments, the segments with minor copy number of 0 are assigned LOH. These segments are either a 1-copy loss, copy-neutral, or a higher order LOH, depending on the tumor purity.

Tumor Purity

To compute tumor purity, an initial tumor purity estimate was obtained from somatic variants and germline B-allele frequencies, which was then refined using a greedy algorithm that evaluates the likelihood of the tumor purity given the tumor-normal coverage log-ratio and B-allele frequency deviations from the normal expectation. The algorithm iterates through a range of tumor-purities surrounding the initial estimate to return the tumor purity with the maximum likelihood.

Loss of Heterozygosity

For estimation of genome-wide loss of heterozygosity (LOH), each SNP was evaluated for LOH based on the germline variant allele fraction and deviation of B-allele frequencies from normal expectation. A binary 0/1 system was used to assign no LOH/LOH and average proportion of genomic bases under LOH was obtained. The number of bases undergoing LOH may be divided by the total number of bases analyzed using a copy number method, such as the method described in this patent, to determine a genome-wide LOH proportion estimate. In one example, the genome-wide LOH proportion estimate may represent LOH in the somatic (cancer) sample that may not be present in the germline (normal) sample.

Average LOH at BRCA1 and BRCA2 genes may be determined in a likewise manner, but considering only the two gene coordinates. In one example, the LOH for BRCA 1/2 genes may represent LOH in the somatic (cancer) sample that may not be present in the germline (normal) sample.

Counting Pathogenic Variant Counts

For counting pathogenic variant counts in specific genes, we used all the SNPs called for each patient, and matched them up with a curated reference mutation list that contains a list of known pathogenic and truncating BRCA variants, e.g., BRCA1 and BRCA2. A pathogenic variant count was then obtained based on the overlap in SNP positions. A separate somatic and germline variant count is also output for BRCA. A sum of the two counts may also be generated.

In some embodiments, the pathogenic variants used in the systems and methods described herein include one or more of the variants listed in Table 1. In some embodiments, the pathogenic variants used in the systems and methods described herein include at least 5, 10, 15, 20, 25, 30, 40, 50, 75, 100, 125, or all of the variants listed in Table 1.

TABLE 1

| Examples of pathogenic BRCA1 and BRCA2 variants | | | | |
| --- | --- | --- | --- | --- |
| Chr | Position | Reference allele | Alternate allele | cpra |
| 13 | 32890558 | G | A | 13_32890558_G_A |
| 13 | 32890593 | TA | T | 13_32890593_TA_T |
| 13 | 32893214 | A | C | 13_32893214_A_C |
| 13 | 32893239 | G | A | 13_32893239_G_A |
| 13 | 32893373 | C | A | 13_32893373_C_A |
| 13 | 32893435 | G | T | 13_32893435_G_T |
| 13 | 32900288 | G | T | 13_32900288_G_T |
| 13 | 32900751 | G | A | 13_32900751_G_A |
| 13 | 32903604 | CTG | C | 13_32903604_CTG_C |
| 13 | 32905165 | AT | A | 13_32905165_AT_A |
| 13 | 32906571 | ATCTACAAAAAG | A | 13_32906571_ATCTACAAAAAG_A |
| 13 | 32906909 | G | T | 13_32906909_G_T |
| 13 | 32907331 | AGCTTT | A | 13_32907331_AGCTTT_A |
| 13 | 32907365 | AAAAAG | A | 13_32907365_AAAAAG_A |
| 13 | 32907408 | CATCTT | C | 13_32907408_CATCTT_C |
| 13 | 32907420 | G | GA | 13_32907420_G_GA |

TABLE 1-continued

Examples of pathogenic BRCA1 and BRCA2 variants

| Chr | Position | Reference allele | Alternate allele | cpra |
|---|---|---|---|---|
| 13 | 32907420 | GA | G | 13_32907420_GA_G |
| 13 | 32910644 | G | T | 13_32910644_G_T |
| 13 | 32910797 | C | CT | 13_32910797_C_CT |
| 13 | 32911001 | GA | G | 13_32911001_GA_G |
| 13 | 32911297 | TAAAC | T | 13_32911297_TAAAC_T |
| 13 | 32911321 | T | TA | 13_32911321_T_TA |
| 13 | 32911356 | AC | A | 13_32911356_AC_A |
| 13 | 32911380 | T | TA | 13_32911380_T_TA |
| 13 | 32911470 | G | A | 13_32911470_G_A |
| 13 | 32911757 | C | T | 13_32911757_C_T |
| 13 | 32911775 | C | T | 13_32911775_C_T |
| 13 | 32911877 | C | T | 13_32911877_C_T |
| 13 | 32911968 | GC | G | 13_32911968_GC_G |
| 13 | 32912089 | CTG | C | 13_32912089_CTG_C |
| 13 | 32912171 | CTG | C | 13_32912171_CTG_C |
| 13 | 32912351 | AATAAT | A | 13_32912351_AATAAT_A |
| 13 | 32912398 | TG | T | 13_32912398_TG_T |
| 13 | 32912503 | TG | T | 13_32912503_TG_T |
| 13 | 32912539 | TCATA | T | 13_32912539_TCATA_T |
| 13 | 32912587 | T | A | 13_32912587_T_A |
| 13 | 32912701 | TTCAAA | T | 13_32912701_TTCAAA_T |
| 13 | 32912703 | C | A | 13_32912703_C_A |
| 13 | 32912735 | G | T | 13_32912735_G_T |
| 13 | 32912770 | A | AT | 13_32912770_A_AT |
| 13 | 32912967 | AAG | A | 13_32912967_AAG_A |
| 13 | 32913118 | GA | G | 13_32913118_GA_G |
| 13 | 32913139 | AG | A | 13_32913139_AG_A |
| 13 | 32913143 | C | T | 13_32913143_C_T |
| 13 | 32913181 | G | A | 13_32913181_G_A |
| 13 | 32913457 | C | G | 13_32913457_C_G |
| 13 | 32913558 | C | CA | 13_32913558_C_CA |
| 13 | 32913648 | A | AT | 13_32913648_A_AT |
| 13 | 32913668 | G | GA | 13_32913668_G_GA |
| 13 | 32913708 | ATTTAAGT | A | 13_32913708_ATTTAAGT_A |
| 13 | 32913836 | CA | C | 13_32913836_CA_C |
| 13 | 32914014 | CA | C | 13_32914014_CA_C |
| 13 | 32914102 | CAGTAA | C | 13_32914102_CAGTAA_C |
| 13 | 32914191 | C | G | 13_32914191_C_G |

TABLE 1-continued

Examples of pathogenic BRCA1 and BRCA2 variants

| Chr | Position | Reference allele | Alternate allele | cpra |
|---|---|---|---|---|
| 13 | 32914209 | ACT | A | 13_32914209_ACT_A |
| 13 | 32914226 | G | T | 13_32914226_G_T |
| 13 | 32914247 | A | T | 13_32914247_A_T |
| 13 | 32914250 | GT | G | 13_32914250_GT_G |
| 13 | 32914349 | G | T | 13_32914349_G_T |
| 13 | 32914437 | GT | G | 13_32914437_GT_G |
| 13 | 32914502 | G | T | 13_32914502_G_T |
| 13 | 32914715 | A | T | 13_32914715_A_T |
| 13 | 32914757 | G | T | 13_32914757_G_T |
| 13 | 32914766 | CTT | C | 13_32914766_CTT_C |
| 13 | 32914851 | C | A | 13_32914851_C_A |
| 13 | 32915135 | TACTC | T | 13_32915135_TACTC_T |
| 13 | 32915292 | C | G | 13_32915292_C_G |
| 13 | 32920978 | C | T | 13_32920978_C_T |
| 13 | 32929238 | TCA | T | 13_32929238_TCA_T |
| 13 | 32929275 | G | T | 13_32929275_G_T |
| 13 | 32929426 | G | A | 13_32929426_G_A |
| 13 | 32931878 | G | A | 13_32931878_G_A |
| 13 | 32936711 | G | A | 13_32936711_G_A |
| 13 | 32936732 | G | C | 13_32936732_G_C |
| 13 | 32936732 | G | T | 13_32936732_G_T |
| 13 | 32936828 | C | A | 13_32936828_C_A |
| 13 | 32936830 | G | A | 13_32936830_G_A |
| 13 | 32937354 | T | TA | 13_32937354_T_TA |
| 13 | 32937354 | TA | T | 13_32937354_TA_T |
| 13 | 32937479 | CA | C | 13_32937479_CA_C |
| 13 | 32937506 | G | C | 13_32937506_G_C |
| 13 | 32944693 | A | G | 13_32944693_A_G |
| 13 | 32950809 | AAC | A | 13_32950809_AAC_A |
| 13 | 32950889 | T | G | 13_32950889_T_G |
| 13 | 32950928 | G | A | 13_32950928_G_A |
| 13 | 32950932 | A | G | 13_32950932_A_G |
| 13 | 32953453 | G | A | 13_32953453_G_A |
| 13 | 32953526 | C | T | 13_32953526_C_T |
| 13 | 32953556 | G | T | 13_32953556_G_T |
| 13 | 32953640 | G | GA | 13_32953640_G_GA |
| 13 | 32953886 | G | A | 13_32953886_G_A |
| 13 | 32953974 | C | G | 13_32953974_C_G |

TABLE 1-continued

Examples of pathogenic BRCA1 and BRCA2 variants

| Chr | Position | Reference allele | Alternate allele | cpra |
| --- | --- | --- | --- | --- |
| 13 | 32954022 | C | CA | 13_32954022_C_CA |
| 13 | 32954022 | CA | C | 13_32954022_CA_C |
| 13 | 32954050 | G | A | 13_32954050_G_A |
| 13 | 32954147 | TC | T | 13_32954147_TC_T |
| 13 | 32954180 | C | T | 13_32954180_C_T |
| 13 | 32954222 | C | T | 13_32954222_C_T |
| 13 | 32954272 | G | GA | 13_32954272_G_GA |
| 13 | 32954272 | GA | G | 13_32954272_GA_G |
| 13 | 32968850 | C | A | 13_32968850_C_A |
| 13 | 32968863 | C | G | 13_32968863_C_G |
| 17 | 41197784 | G | A | 17_41197784_G_A |
| 17 | 41199658 | A | T | 17_41199658_A_T |
| 17 | 41203122 | G | GC | 17_41203122_G_GC |
| 17 | 41209079 | T | TG | 17_41209079_T_TG |
| 17 | 41209154 | T | C | 17_41209154_T_C |
| 17 | 41215362 | TTTTC | T | 17_41215362_TTTTC_T |
| 17 | 41215948 | G | A | 17_41215948_G_A |
| 17 | 41223097 | G | A | 17_41223097_G_A |
| 17 | 41223176 | TG | T | 17_41223176_TG_T |
| 17 | 41223242 | G | C | 17_41223242_G_C |
| 17 | 41226411 | G | A | 17_41226411_G_A |
| 17 | 41226447 | CTT | C | 17_41226447_CTT_C |
| 17 | 41234421 | CT | C | 17_41234421_CT_C |
| 17 | 41234451 | G | A | 17_41234451_G_A |
| 17 | 41243479 | CTTGA | C | 17_41243479_CTTGA_C |
| 17 | 41243533 | C | A | 17_41243533_C_A |
| 17 | 41243704 | C | A | 17_41243704_C_A |
| 17 | 41243800 | C | A | 17_41243800_C_A |
| 17 | 41243843 | GTTTAC | G | 17_41243843_GTTTAC_G |
| 17 | 41244281 | CA | C | 17_41244281_CA_C |
| 17 | 41244614 | A | C | 17_41244614_A_C |
| 17 | 41244865 | GTT | G | 17_41244865_GTT_G |
| 17 | 41244913 | C | A | 17_41244913_C_A |
| 17 | 41245161 | G | GT | 17_41245161_G_GT |
| 17 | 41245203 | CT | C | 17_41245203_CT_C |
| 17 | 41245330 | CTT | C | 17_41245330_CTT_C |
| 17 | 41245513 | T | A | 17_41245513_T_A |
| 17 | 41245586 | CT | C | 17_41245586_CT_C |

TABLE 1-continued

Examples of pathogenic BRCA1 and BRCA2 variants

| Chr | Position | Reference allele | Alternate allele | cpra |
|---|---|---|---|---|
| 17 | 41245603 | C | A | 17_41245603_C_A |
| 17 | 41245834 | C | A | 17_41245834_C_A |
| 17 | 41245888 | C | A | 17_41245888_C_A |
| 17 | 41246186 | ACT | A | 17_41246186_ACT_A |
| 17 | 41246197 | AT | A | 17_41246197_AT_A |
| 17 | 41246278 | CAG | C | 17_41246278_CAG_C |
| 17 | 41246531 | CT | C | 17_41246531_CT_C |
| 17 | 41246539 | C | A | 17_41246539_C_A |
| 17 | 41246723 | G | GCCACATGGCT | 17_41246723_G_GCCACATGGCT |
| 17 | 41247864 | C | CT | 17_41247864_C_CT |
| 17 | 41247940 | C | A | 17_41247940_C_A |
| 17 | 41256203 | TG | T | 17_41256203_TG_T |
| 17 | 41258504 | A | C | 17_41258504_A_C |
| 17 | 41267762 | A | G | 17_41267762_A_G |
| 17 | 41276044 | ACT | A | 17_41276044_ACT_A |
| 17 | 41276048 | TAA | T | 17_41276048_TAA_T |

Positive HRD Calls Based on HRD Markers

In various aspects, if certain markers of HRD are detected, the systems and methods disclosed herein return a positive HRD call. In one example, if a pathogenic stop gain or frameshift variant is present in BRCA1 or BRCA2 a positive HRD call is returned. In another example, if genome-wide loss of heterozygosity proportion is above the threshold indicative of BRCA mutation, combined with loss of heterozygosity of BRCA1 or BRCA2, a positive HRD call is returned.

Classifiers

Generally, many different classification algorithms find use in the systems and methods described herein. For instance, in some embodiments, the model is a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

In some embodiments, the classification algorithm used in the systems and methods described herein is a random forest algorithm. In some embodiments, the trained classification method comprises a trained classifier stream. In some embodiments, by way of non-limiting example the trained classifier stream is a decision tree. Decision tree algorithms suitable for use as the classification models described herein are described in, for example, Duda, 2001, Pattern Classification, John Wiley & Sons, Inc., New York, 395-396, which is hereby incorporated by reference. Tree-based methods partition the feature space into a set of rectangles, and then fit a model (like a constant) in each one. In some embodiments, the decision tree is random forest regression. One specific algorithm that can be used as the classification model is a classification and regression tree (CART). Other examples of specific decision tree algorithms that can be used as the classifier include, but are not limited to, ID3, C4.5, MART, and Random Forests. CART, ID3, and C4.5 are described in Duda, 2001, Pattern Classification, John Wiley & Sons, Inc., New York. 396-408 and 411-412, which is hereby incorporated by reference. CART, MART, and C4.5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety.

In some embodiments, tumor organoids with varied BRCA LOH statuses, pathogenic mutations and genome-wide LOH measurements may be grown and treated with PARP inhibitors to obtain an in-vitro PARP drug response. Samples could span a wide range of cancer cohorts. Tumor cell lines expected to be PARP sensitive may be tested alongside negative controls that have no HRD mutations. The PARP outcome data may be used to refine input features in the random forest classifier. Additional information could be gleaned from mutational signatures and other genes in the HRD pathway. See, for example, Gulhan D C, Lee J J, Melloni G E M, Cortés-Ciriano I, Park P J, "Detecting the mutational signature of homologous recombination deficiency in clinical samples," Nat Genet., 51 (5): 912-19 (2019), which is incorporated by reference herein.

Figure 10A:
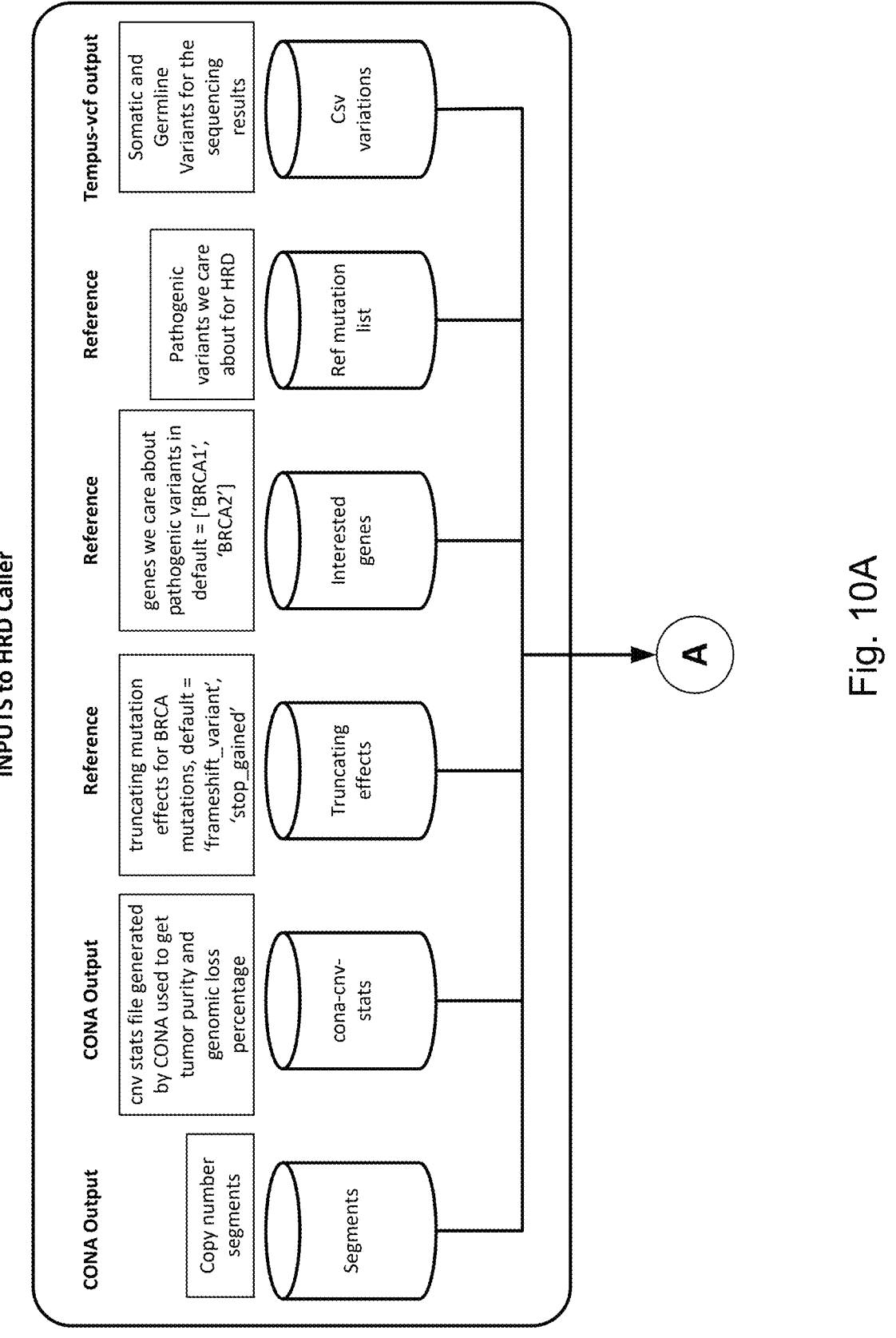
FIGS. 10A and 10B collectively illustrate an example system for generating HRD calls and the necessary output, in accordance with some embodiments of the present disclosure.
Figure 10B:
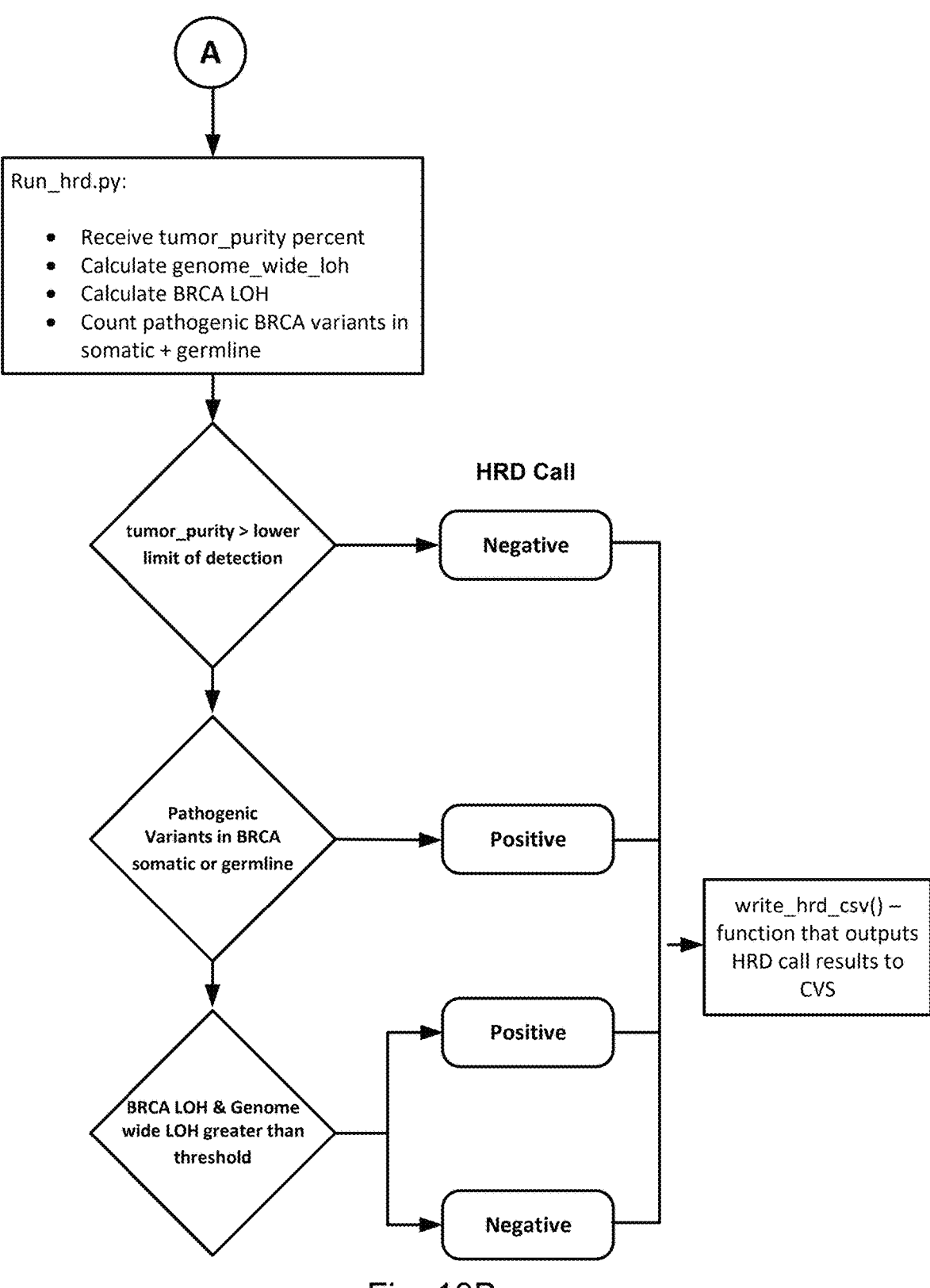

In an alternative embodiment, instead of or in addition to training a random forest classifier to generate HRD calls, the systems and methods use business logic. For example, in some embodiments, a business rule set, such as is illustrated in FIG. 10, is used in the systems and methods described herein.

In some embodiments, the classification algorithm used the systems and methods described herein is a regression algorithm. The regression algorithm can be any type of regression. For example, in some embodiments, the regression algorithm is logistic regression. Logistic regression algorithms are disclosed in Agresti, An Introduction to Categorical Data Analysis, 1996, Chapter 5, pp. 103-144, John Wiley & Son, New York, which is hereby incorporated by reference. In some embodiments, the regression algorithm is logistic regression with lasso, L2 or elastic net regularization.

In some embodiments, the classification algorithm used the systems and methods described herein is a neural network. Examples of neural network algorithms, including convolutional neural network algorithms, are disclosed, for example, in Vincent et al., 2010, "Stacked denoising auto-encoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference.

In some embodiments, the classification algorithm used the systems and methods described herein is a support vector machine (SVM). Examples of SVM algorithms are described, for example, in Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety. When used for classification, SVMs separate a given set of binary labeled data training set with a hyper-plane that is maximally distant from the labeled data. For cases in which no linear separation is possible, SVMs can work in combination with the technique of "kernels," which automatically realizes a non-linear mapping to a feature space. The hyper-plane found by the SVM in feature space corresponds to a non-linear decision boundary in the input space.

In some embodiments, the machine-learned model includes a logistic regression classifier. In other embodiments, the machine learning or deep learning model can be one of a decision tree, an ensemble (e.g., bagging, boosting, random forest), gradient boosting machine, linear regression, Naïve Bayes, or a neural network. The HRD model includes learned weights for the features that are adjusted during training. The term "weights" is used generically here to represent the learned quantity associated with any given feature of a model, regardless of which particular machine learning technique is used. In some embodiments, a cancer indicator score is determined by inputting values for features derived from one or more DNA sequences (or DNA sequence reads thereof) into a machine learning or deep learning model.

In some embodiments, e.g., when the HRD evaluation model is a neural network (e.g., a conventional or convolutional neural network), the output of a disease classifier is a classification, e.g., either cancer positive or cancer negative. However, in some embodiments, in order to provide a continuous or semi-continuous value for the output of the model, rather than a classification, a hidden layer of a neural network, e.g., the hidden layer just prior to the output layer, is used as the output of the classification model.

Accordingly, in some embodiments, the model includes (i) an input layer for receiving values for the plurality of genotypic characteristics, where the plurality of genotypic characteristics includes a first number of dimensions, and (ii) an embedding layer that includes a set of weights, where the embedding layer directly or indirectly receives output of the input layer, and where an output of the embedding layer is a model score set having a second number of dimensions that is less than the first number of dimensions, and (iii) an output layer that directly or indirectly receives the model score set from the embedding layer. In some embodiments, the output of the classifier is an output of a set of neurons associated with a hidden layer in a neural network termed the embedding layer. In such embodiments, each such neuron in the embedding layer is associated with a weight and an activation function and the output consists of the output of each such activation function. In some embodiments, the activation function of a neuron in the embedding layer is rectified linear unit (ReLU), tanh, or sigmoid activation function. In some such embodiments, the neurons of the embedding layer are fully connected to each of the inputs of the input layer. In some such embodiments, each neuron of the output layer is fully connected to each neuron of the embedding layer. In some embodiments, each neuron of the output layer is associated with a Softmax activation function. In some embodiments, one or more of the embedding layer and the output layer is not fully connected.

Patient Report

In some embodiments, a patient report is generated based on the output of the classifier. The report may be presented to a patient, physician, medical personnel, or researcher in a digital copy (for example, a JSON object, pdf file or an image on a website or portal), a hard copy (for example, printed on paper or another tangible medium), or in another format.

In some embodiments, the report includes information related to the HRD status of the specimen, detected genetic variants, other characteristics of a patient's sample, and/or clinical records. The report may further include clinical trials for which the patient is eligible, therapies that may match the patient and/or adverse effects predicted if the patient receives a given therapy, based on the HRD status, detected genetic variants, other characteristics of the sample and/or clinical records. In one example, if a patient specimen is predicted to have HRD, the patient may be matched with PARP inhibitors, platinum-based chemotherapy, and/or additional DNA-damaging therapies.

The results included in the report and/or additional results (for example, from the bioinformatics pipeline) may be used to analyze a database of clinical data, especially to determine whether there is a trend showing that a therapy slowed cancer progression in other patients having the same or similar results as the specimen. The results may also be used to design tumor organoid experiments. For example, an organoid may be genetically engineered to have the same characteristics as the specimen and may be observed after exposure to a therapy to determine whether the therapy can reduce the growth rate of the organoid, and thus is likely to reduce the growth rate of the patient associated with the specimen.

In this example, HRD information may be stored in a report object, such as a JSON object, for further processing and/or display. For example, information from the report object may be used to prepare a clinical laboratory report for return to an ordering physician. The information may be provided as a combination of text, images, and/or audio. An example display of text and images that indicate HRD information is presented as FIG. 11.

In some embodiments, the report also includes a listing of genetic variants related to the genes in the homologous recombination DNA repair pathway and/or genes that interact with this pathway. An example display for this listing is presented as FIG. 12.

Therapy

In some aspects, the systems and methods disclosed herein may be used as a companion diagnostic. For example, in some embodiments, an estimated HRD status may be used by a clinician to make a decision to treat a cancer with a PARP inhibitor.

Table 2 lists several PARP inhibitors and the FDA approval or clinical trial status of each PARP inhibitor for various cancer types in 2019. This table illustrates the widespread potential utility of PARP inhibitors for patients who have tested positive for HRD.

TABLE 2

| Example PARP inhibitors | | |
| --- | --- | --- |
| Drug | Cancer Types | FDA Approval |
| Olaparib | Ovarian, Breast | Approved |
| | Gastric, Gastroesophageal Junction, Prostate, Lung (SC/NSC), Pancreatic Fallopian, Primary Peritoneal, Urothelial (Bladder), Pediatric Solid Tumors & Non-Hodgkin's | Trial |
| Rucaparib | Ovarian | Approved |
| | Fallopian, Primary Peritoneal, Any BRCA1/2 Solid, Urothelial, Prostate, Endometrial | Trial |
| Niraparib | Ovarian, Fallopian, Primary Peritoneal | Approved |
| | Pancreatic, Prostate, Solid | Trial |
| Talazoparib | Breast | Approved |
| | Advanced or Recurrent Solid Tumors, Breast Neoplasms, Epithelial Ovarian Cancer, Ewing Sarcoma, Small Cell Lung Carcinoma, Prostate Cancer, Pancreas Cancer | Trial |

In some aspects, an estimated HRD status may be used by a clinician to make a decision to treat a cancer with the addition of platinum to standard neoadjuvant chemotherapy. Adding a platinum agent to standard combination chemotherapy increases the toxicity of treatment, and so patients will benefit from an estimated HRD that indicates whether their cancer is more likely to be treated through the combination of a platinum agent and standard combination chemotherapy.

In some aspects, PARP inhibitors have been approved for treatment of cancers harboring specifically germline alterations. For example, olaparib is approved for germline BRCA (gBRCA) positive ovarian cancer treated with at least 3 prior chemo regimens and talazoparib is approved for gBRCA positive, HER2 negative localized or metastatic breast cancer. Detecting germline variants in BRCA or other genes related to DNA repair pathways may aid a physician in deciding to prescribe PARPi.

Implementation Using a Digital and Laboratory Health Care Platform

The methods and systems described herein may be utilized in combination with or as part of a digital and laboratory health care platform that is generally targeted to medical care and research. It should be understood that many uses of the methods and systems described above, in combination with such a platform, are possible. One example of such a platform is described in U.S. patent application Ser. No. 16/657,804, titled "Data Based Cancer Research and Treatment Systems and Methods", and filed Oct. 18, 2019, which is incorporated herein by reference and in its entirety for all purposes.

For example, an implementation of one or more embodiments of the methods and systems as described above may include microservices constituting a digital and laboratory health care platform supporting HRD detection. Embodiments may include a single microservice for executing and delivering _____ or may include a plurality of microservices each having a particular role which together implement one or more of the embodiments above. In one example, a first microservice may execute computation of genomic features in order to deliver features to a second microservice for training an HRD model. Similarly, the second microservice may execute training an HRD model to deliver a trained HRD model to a third microservice according to an embodiment, above. A third microservice may use a trained HRD model to analyze data associated with a specimen to determine the likelihood of the specimen having HRD.

Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above. A micro-services based order management system is disclosed, for example, in U.S. Prov. Patent Application No. 62/873,693, titled "Adaptive Order Fulfillment and Tracking Methods and Systems", filed Jul. 12, 2019, which is incorporated herein by reference and in its entirety for all purposes.

For example, continuing with the above first and second microservices, an order management system may notify the first microservice that an order for _____ has been received and is ready for processing. The first microservice may execute and notify the order management system once the delivery of _____ is ready for the second microservice. Furthermore, the order management system may identify that execution parameters (prerequisites) for the second microservice are satisfied, including that the first microservice has completed, and notify the second microservice that it may continue processing the order to _____ according to an embodiment, above.

Where the digital and laboratory health care platform further includes a genetic analyzer system, the genetic analyzer system may include targeted panels and/or sequencing probes. An example of a targeted panel is disclosed, for example, in U.S. Prov. Patent Application No. 62/902,950, titled "System and Method for Expanding Clinical Options for Cancer Patients using Integrated Genomic Profiling", and filed Sep. 19, 2019, which is incorporated herein by reference and in its entirety for all purposes. In one example, targeted panels may enable the delivery of next generation sequencing results _____ for according to an embodiment, above. An example of the design of next-generation sequencing probes is disclosed, for example, in U.S. Prov. Patent Application No. 62/924, 073, titled "Systems and Methods for Next Generation Sequencing Uniform Probe Design", and filed Oct. 21, 2019, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome. The methods and systems described above may be utilized, for example, to ingest the DNA and/or RNA read counts and produce _____ as a result.

When the digital and laboratory health care platform further includes an RNA data normalizer, any RNA read counts may be normalized before processing embodiments as described above. An example of an RNA data normalizer is disclosed, for example, in U.S. patent application Ser. No. 16/581,706, titled "Methods of Normalizing and Correcting RNA Expression Data", and filed Sep. 24, 2019, which is incorporated herein by reference and in its entirety for all purposes.

When the digital and laboratory health care platform further includes a genetic data deconvoluter, any system and method for deconvoluting may be utilized for analyzing genetic data associated with a specimen having two or more biological components to determine the contribution of each component to the genetic data and/or determine what genetic data would be associated with any component of the specimen if it were purified. An example of a genetic data deconvoluter is disclosed, for example, in U.S. patent application Ser. No. 16/732,229 and PCT19/69161, both titled "Transcriptome Deconvolution of Metastatic Tissue Samples", and filed Dec. 31, 2019, U.S. Prov. Patent Application No. 62/924,054, titled "Calculating Cell-type RNA Profiles for Diagnosis and Treatment", and filed Oct. 21, 2019, and U.S. Prov. Patent Application No. 62/944,995, titled "Rapid Deconvolution of Bulk RNA Transcriptomes for Large Data Sets (Including Transcriptomes of Specimens Having Two or More Tissue Types)", and filed Dec. 6, 2019 which are incorporated herein by reference and in their entirety for all purposes.

When the digital and laboratory health care platform further includes an automated RNA expression caller, RNA expression levels may be adjusted to be expressed as a value relative to a reference expression level, which is often done in order to prepare multiple RNA expression data sets for analysis to avoid artifacts caused when the data sets have differences because they have not been generated by using the same methods, equipment, and/or reagents. An example of an automated RNA expression caller is disclosed, for example, in U.S. Prov. Patent Application No. 62/943,712, titled "Systems and Methods for Automating RNA Expression Calls in a Cancer Prediction Pipeline", and filed Dec. 4, 2019, which is incorporated herein by reference and in its entirety for all purposes.

The digital and laboratory health care platform may further include one or more insight engines to deliver information, characteristics, or determinations related to a disease state that may be based on genetic and/or clinical data associated with a patient and/or specimen. Exemplary insight engines may include a tumor of unknown origin engine, a human leukocyte antigen (HLA) loss of homozy-gosity (LOH) engine, a tumor mutational burden engine, a PD-L1 status engine, a homologous recombination deficiency engine, a cellular pathway activation report engine, an immune infiltration engine, a microsatellite instability engine, a pathogen infection status engine, and so forth. An example tumor of unknown origin engine is disclosed, for example, in U.S. Prov. Patent Application No. 62/855,750, titled "Systems and Methods for Multi-Label Cancer Classification", and filed May 31, 2019, which is incorporated herein by reference and in its entirety for all purposes. An example of an HLA LOH engine is disclosed, for example, in U.S. Prov. Patent Application No. 62/889,510, titled "Detection of Human Leukocyte Antigen Loss of Heterozygosity", and filed Aug. 20, 2019, which is incorporated herein by reference and in its entirety for all purposes. An example of a tumor mutational burden (TMB) engine is disclosed, for example, in U.S. Prov. Patent Application No. 62/804,458, titled "Assessment of Tumor Burden Methodologies for Targeted Panel Sequencing", and filed Feb. 12, 2019, which is incorporated herein by reference and in its entirety for all purposes. An example of a PD-L1 status engine is disclosed, for example, in U.S. Prov. Patent Application No. 62/854,400, titled "A Pan-Cancer Model to Predict The PD-L1 Status of a Cancer Cell Sample Using RNA Expression Data and Other Patient Data", and filed May 30, 2019, which is incorporated herein by reference and in its entirety for all purposes. An additional example of a PD-L1 status engine is disclosed, for example, in U.S. Prov. Patent Application No. 62/824,039, titled "PD-L1 Prediction Using H&E Slide Images", and filed Mar. 26, 2019, which is incorporated herein by reference and in its entirety for all purposes. The systems and methods disclosed herein are an example of a homologous recombination deficiency engine. An alternative homologous recombination deficiency engine is disclosed, for example, in U.S. Prov. Patent Application No. 62/804,730, titled "An Integrative Machine-Learning Framework to Predict Homologous Recombination Deficiency", and filed Feb. 12, 2019, which is incorporated herein by reference and in its entirety for all purposes. An example of a cellular pathway activation report engine is disclosed, for example, in U.S. Prov. Patent Application No. 62/888,163, titled "Cellular Pathway Report", and filed Aug. 16, 2019, which is incorporated herein by reference and in its entirety for all purposes. An example of an immune infiltration engine is disclosed, for example, in U.S. patent application Ser. No. 16/533,676, titled "A Multi-Modal Approach to Predicting Immune Infiltration Based on Integrated RNA Expression and Imaging Features", and filed Aug. 6, 2019, which is incorporated herein by reference and in its entirety for all purposes. An additional example of an immune infiltration engine is disclosed, for example, in U.S. Patent Application No. 62/804,509, titled "Comprehensive Evaluation of RNA Immune System for the Identification of Patients with an Immunologically Active Tumor Microenvironment", and filed Feb. 12, 2019, which is incorporated herein by reference and in its entirety for all purposes. An example of an MSI engine is disclosed, for example, in U.S. patent application Ser. No. 16/653,868, titled "Microsatellite Instability Determination System and Related Methods", and filed Oct. 15, 2019, which is incorporated herein by reference and in its entirety for all purposes. An additional example of an MSI engine is disclosed, for example, in U.S. Prov. Patent Application No. 62/931,600, titled "Systems and Methods for Detecting Microsatellite Instability of a Cancer Using a Liquid Biopsy", and filed Nov. 6, 2019, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ. The report may include therapies and/or clinical trials matched based on a portion or all of the genetic profile or insight engine findings and summaries. For example, the therapies may be matched according to the systems and methods disclosed in U.S. Prov. Patent Application No. 62/804,724, titled "Therapeutic Suggestion Improvements Gained Through Genomic Biomarker Matching Plus Clinical History", filed Feb. 12, 2019, which is incorporated herein by reference and in its entirety for all purposes. For example, the clinical trials may be matched according to the systems and methods disclosed in U.S. Prov. Patent Application No. 62/855,913, titled "Systems and Methods of Clinical Trial Evaluation", filed May 31, 2019, which is incorporated herein by reference and in its entirety for all purposes.

The report may include a comparison of the results to a database of results from many specimens. An example of methods and systems for comparing results to a database of results are disclosed in U.S. Prov. Patent Application No. 62/786,739, titled "A Method and Process for Predicting and Analyzing Patient Cohort Response, Progression and Survival", and filed Dec. 31, 2018, which is incorporated herein by reference and in its entirety for all purposes. The information may be used, sometimes in conjunction with similar information from additional specimens and/or clinical response information, to discover biomarkers or design a clinical trial.

When the digital and laboratory health care platform further includes application of one or more of the embodiments herein to organoids developed in connection with the platform, the methods and systems may be used to further evaluate genetic sequencing data derived from an organoid to provide information about the extent to which the organoid that was sequenced contained a first cell type, a second cell type, a third cell type, and so forth. For example, the report may provide a genetic profile for each of the cell types in the specimen. The genetic profile may represent genetic sequences present in a given cell type and may include variants, expression levels, information about gene products, or other information that could be derived from genetic analysis of a cell. The report may include therapies matched based on a portion or all of the deconvoluted information. These therapies may be tested on the organoid, derivatives of that organoid, and/or similar organoids to determine an organoid's sensitivity to those therapies. For example, organoids may be cultured and tested according to the systems and methods disclosed in U.S. patent application Ser. No. 16/693,117, titled "Tumor Organoid Culture Compositions, Systems, and Methods", filed Nov. 22, 2019; U.S. Prov. Patent Application No. 62/924,621, titled "Systems and Methods for Predicting Therapeutic Sensitivity", filed Oct. 22, 2019; and U.S. Prov. Patent Application No. 62/944, 292, titled "Large Scale Phenotypic Organoid Analysis", filed Dec. 5, 2019, which are incorporated herein by reference and in their entirety for all purposes.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Provisional Patent Application No. 62/924,515, titled "Artificial Intelligence Assisted Precision Medicine Enhancements to Standardized Laboratory Diagnostic Testing", and filed Oct. 22, 2019, which is incorporated herein by reference and in its entirety for all purposes.

It should be understood that the examples given above are illustrative and do not limit the uses of the systems and methods described herein in combination with a digital and laboratory health care platform.

EXAMPLES

Example 1—Analysis of an Initial HRD Prediction Model

The accuracy of an initial HRD prediction algorithm, as described herein, was evaluated using a small 40 sample training set curated with samples having known pathogenic mutations in BRCA. All the genomic features needed for HRD prediction were computed on the training samples using CONA. The sklearn 'train_test_split' method was used to create training and test sets for initial validation. The sklearn 'standard scaler' and 'fit_transform' method was used to normalize the mean and variance in training samples and also to keep the future test data scale identical. The 'RandomForestClassifier' method was used to create a random forest classifier with the number of genomic features set as 'n_estimators'. Using the 'compute_simple_cross_val_score' we computed a simple 5-fold cross validation score metric and obtained a 99% classification accuracy. Top k-features were obtained using the standard Gini criterion. We used pickle to dump the classification model to a file, and loaded the model to make predictions for each test sample. For each patient, we first computed the HRD features using CONA, and standardized the features using the same scaling function used for the training samples. The probability of HRD was then obtained given these standardized features using the 'model.predict_proba' function implemented in sklearn. The confidence in HRD prediction is the model prediction probability, and a positive call is defined for samples with probability >0.5. Any new features can easily be incorporated into this model, and the training set can be easily expanded for re-training and prediction.

Example 2—Analysis of an Initial HRD Prediction Model

The HRD status of 1000 patient samples across 35 different cancer-types were analyzed using an HRD classifier as described herein. The analysis identified a total 6.4% HRD-positive calls. Pathogenic variants in BRCA genes were significantly greater in HRD-positive calls than negative calls (P<4.1e-219, Mann-Whitney test), while LOH in BRCA was not enriched (P<0.06, Mann-Whitney test). Ovarian cancer (12% HRD-positive, n=57), breast cancer (14.6%, n=89), and colorectal cancer (10%, n=285) were some of the most-represented cancer types. Contrary to previously-published results, few patients with pancreatic (2.3%, n=295) and prostate (2.7%, n=37) had predicted HRD.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in any combination in FIG. 1 and/or as described elsewhere within the application. These program modules can be stored on a CD-ROM, DVD, magnetic disk storage product, USB key, or any other non-transitory computer readable data or program storage product.

Many modifications and variations of this disclosure can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The disclosure is to be limited only by the terms of the appended claims, along with the full scope of equivalents to which such claims are entitled.

subject and a second plurality of sequence reads of a second DNA sample from a non-cancerous tissue of the subject, a set of genomic data for the test subject comprising:
(i) a heterozygosity status for a first plurality of DNA damage repair genes in the genome of the cancerous tissue of the subject, wherein the heterozygosity status derives from a count of a number of unique frameshift mutations or a number of unique truncating mutations detected in the first plurality of DNA damage repair genes in the genome of the cancerous tissue of the subject,
(ii) a measure of the loss of heterozygosity, on a proportionate scale, across the genome of the cancerous tissue of the subject,
(iii) a first measure of variant alleles detected in a second plurality of DNA damage repair genes in the genome of the cancerous tissue of the subject, wherein the first measure of variant alleles derives from a first count of a number of unique mutations associated with a loss of homologous recombination detected in the second plurality of DNA damage repair genes in the genome of the cancerous tissue of the subject, and
(iv) a second measure of variant alleles detected in the second plurality of DNA damage repair genes in the genome of the non-cancerous tissue of the subject, wherein the second measure of variant alleles derives from a second count of a number of unique mutations associated with loss of homologous recombination detected in the second plurality of DNA damage repair genes in the genome of the cancerous tissue of the subject;
(B) determining a measure of tumor purity in the test subject using the first plurality of sequence reads;

---

---

What is claimed is:
1. A method of determining a homologous recombination deficiency (HRD) status of a test subject afflicted with a cancer, the method comprising:
    at a computer system having one or more processors, and memory storing one or more programs for execution by the one or more processors:
    (A) generating, based on a first plurality of sequence reads of a first DNA sample from a cancerous tissue of the

(C) using the tumor purity in the test subject to verify that the tumor purity in the test subject satisfies a tumor purity threshold;

(D) applying a scaling construct to the set of genomic data thereby obtaining a scaled set of genomic data, wherein the scaling construct is derived from normalization of the set of genomic data from each subject in a training cohort of subjects, wherein the training cohort of subjects includes a first subset of subjects having HRD and a second subject of subjects free of HRD; and (E) inputting, after the using (C), the scaled set of genomic data into a classifier thereby determining a probability that the test subject has HRD.

2. The method of claim 1, wherein the first DNA sample is from a solid tumor biopsy of the cancerous tissue of the subject.

3. The method of claim 1, wherein the second DNA sample is from a buffy coat preparation of a blood sample from the subject.

4. The method of claim 1, the method further comprising performing targeted sequencing using a plurality of nucleic acid probes to enrich nucleic acids from the cancerous tissue of the subject for a panel of genomic regions to generate the first plurality of sequence reads.

5. The method of claim 1, the method further comprising performing whole genome sequencing of nucleic acids from the cancerous tissue of the subject to generate the first plurality of sequence reads.

6. The method of claim 1, the method further comprising performing targeted sequencing using a plurality of nucleic acid probes to enrich nucleic acids from the non-cancerous tissue of the subject for a panel of genomic regions to generate the second plurality of sequence reads.

7. The method of claim 1, the method further comprising performing whole genome sequencing of nucleic acids from the non-cancerous tissue of the subject to generate the second plurality of sequence reads.

8. The method of claim 1, the method further comprising determining the measure of the loss of heterozygosity, on the proportionate scale, across the genome of the cancerous tissue of the subject is determined by:

determining a loss of genomic heterozygosity in the first plurality of sequence reads, and normalizing the determined loss of heterozygosity by an estimate of the tumor purity for the first plurality of sequence reads, wherein the estimate of the tumor purity is based on the first plurality of sequence reads and the second plurality of sequence reads.

9. The method of claim 1, wherein the first plurality of DNA damage repair genes comprises BRCA1 and BRCA2.

10. The method of claim 1, wherein the second plurality of DNA damage repair genes comprises BRCA1 and BRCA2.

11. The method of claim 10, wherein the unique mutations associated with loss of homologous recombination in BRCA1 and BRCA2 include at least 50 of the mutations selected from the group consisting of:

13_32890558_G_A, 13_32890593_TA_T, 13_32893214_A_C, 13_32893239_G_A, 13_32893373_C_A, 13_32893435_G_T, 13_32900288_G_T, 13_32900751_G_A, 13_32903604_CTG_C, 13_32905165_AT_A, 13_32906571_ATCTACAAAAAG_A, 13_32906909_ G_T, 13_32907331_AGCTTT_A, 13_32907365_ AAAAAG_A, 13_32907408_CATCTT_C, 13_32907420_G_GA, 13_32907420_GA_G, 13_32910644_G_T, 13_32910797_C_CT, 13_32911001_GA_G, 13_32911297_TAAAC_T, 13_32911321_T_TA, 13_32911356_AC_A, 13_32911380_T_TA, 13_32911470_G_A, 13_32911757_C_T, 13_32911775_C_T, 13_32911877_C_T, 13_32911968_GC_G, 13_32912089_CTG_C, 13_32912171_CTG_C, 13_32912351_AATAAT_A, 13_32912398_TG_T, 13_32912503_TG_T, 13_32912539_TCATA_T,

13_32912587_T_A, 13_32912701_TTCAAAT, 13_32912703_C_A, 13_32912735_G_T, 13_32912770_A_AT, 13_32912967_AAG_A, 13_32913118_GA_G, 13_32913139_AG_A, 13_32913143_C_T, 13_32913181_G_A, 13_32913457_C_G, 13_32913558_C_CA, 13_32913648_A_AT, 13_32913668_G_GA, 13_32913708_ATTTAAGT_A, 13_32913836_CA_C, 13_32914014_CA_C, 13_32914102_CAGTAA_C, 13_32914191_C_G, 13_32914209_ACT_A, 13_32914226_G_T, 13_32914247_A_T, 13_32914250_GT_G, 13_32914349_G_T, 13_32914437_GT_G, 13_32914502_G_T, 13_32914715_A_T, 13_32914757_G_T, 13_32914766_CTT_C, 13_32914851_C_A, 13_32915135_TACTC_T, 13_32915292_C_G, 13_32920978_C_T, 13_32929238_TCA_T, 13_32929275_G_T, 13_32929426_G_A, 13_32931878_G_A, 13_32936711_G_A, 13_32936732_G_C, 13_32936732_G_T, 13_32936828_C_A, 13_32936830_G_A, 13_32937354_T_TA, 13_32937354_TA_T, 13_32937479_CA_C, 13_32937506_G_C, 13_32944693_A_G, 13_32950809_AAC_A, 13_32950889_T_G, 13_32950928_G_A, 13_32950932_A_G, 13_32953453_G_A, 13_32953526_C_T, 13_32953556_G_T, 13_32953640_G_GA, 13_32953886_G_A, 13_32953974_C_G, 13_32954022_C_CA, 13_32954022_CA_C, 13_32954050_G_A, 13_32954147_TC T, 13_32954180_C_T, 13_32954222_C_T, 13_32954272_G_GA, 13_32954272_GA_G, 13_32968850_C_A, 13_32968863_C_G, 17_41197784_G_A, 17_41199658_A_T, 17_41203122_G_GC, 17_41209079_T_TG, 17_41209154_T_C, 17_41215362_TTTTC_T, 17_41215948_G_A, 17_41223097_G_A, 17_41223176_TG_T, 17_41223242_G_C, 17_41226411_G_A, 17_41226447_CTT_C, 17_41234421_CT_C, 17_41234451_G_A, 17_41243479_CTTGA_C, 17_41243533_C_A, 17_41243704_C_A, 17_41243800_C_A, 17_41243843_GTTTAC_G, 17_41244281_CA_C, 17_41244614_A_C, 17_41244865_GTT_G, 17_41244913_C_A, 17_41245161_G_GT, 17_41245203_CT_C, 17_41245330_CTT_C, 17_41245513_T_A, 17_41245586_CT_C, 17_41245603_C_A, 17_41245834_C_A, 17_41245888_C_A, 17_41246186_ACT_A, 17_41246197_AT_A, 17_41246278_CAG_C, 17_41246531_CT_C, 17_41246539_C_A, 17_41246723_G_GCCA- CATGGCT, 17_41247864_C_CT, 17_41247940_C_A, 17_41256203_TG_T, 17_41258504_A_C, 17_41267762_A_G, 17_41276044_ACT_A, and 17_41276048_TAA_T.

12. The method of claim 10, wherein the unique mutations associated with loss of homologous recombination in BRCA1 and BRCA2 comprises the mutations selected from the group consisting of:

13_32890558_G_A, 13_32890593_TA_T, 13_32893214_A_C, 13_32893239_G_A, 13_32893373_C_A, 13_32893435_G_T, 13_32900288_G_T, 13_32900751_G_A, 13_32903604_CTG_C, 13_32905165_AT_A, 13_32906571 ATCTACAAAAAG_A, 13_32906909_ G_T, 13_32907331_AGCTTT_A, 13_32907365_

AAAAAG_A, 13_32907408_CATCTT_C,
13_32907420_G_GA, 13_32907420_GA_G,
13_32910644_G_T, 13_32910797_C_CT,
13_32911001_GA_G, 13_32911297_TAAAC_T,
13_32911321_T_TA, 13_32911356_AC_A,
13_32911380_T_TA, 13_32911470_G_A,
13_32911757_C_T, 13_32911775_C_T,
13_32911877_C_T, 13_32911968_GC_G,
13_32912089_CTG_C, 13_32912171_CTG_C,
13_32912351_AATAAT_A, 13_32912398_TG_T,
13_32912503_TG_T, 13_32912539_TCATA_T,
13_32912587_T_A, 13_32912701_TTCAAA T,
13_32912703_C_A, 13_32912735_G_T,
13_32912770_A_AT, 13_32912967_AAG_A,
13_32913118_GA_G, 13_32913139_AG_A,
13_32913143_C_T, 13_32913181_G_A,
13_32913457_C_G, 13_32913558_C_CA,
13_32913648_A_AT, 13_32913668_G_GA,
13_32913708_ATTTAAGT_A, 13_32913836_CA_C,
13_32914014_CA_C, 13_32914102_CAGTAA_C,
13_32914191_C_G, 13_32914209_ACT_A,
13_32914226_G_T, 13_32914247_A_T,
13_32914250_GT_G, 13_32914349_G_T,
13_32914437_GT_G, 13_32914502_G_T,
13_32914715_A_T, 13_32914757_G_T,
13_32914766_CTT_C, 13_32914851_C_A,
13_32915135_TACTC_T, 13_32915292_C_G,
13_32920978_C_T, 13_32929238_TCA_T,
13_32929275_G_T, 13_32929426_G_A,
13_32931878_G_A, 13_32936711_G_A,
13_32936732_G_C, 13_32936732_G_T,
13_32936828_C_A, 13_32936830_G_A,
13_32937354_T_TA, 13_32937354_TA_T,
13_32937479_CA_C, 13_32937506_G_C,
13_32944693_A_G, 13_32950809_AAC_A,
13_32950889_T_G, 13_32950928_G_A,
13_32950932_A_G, 13_32953453_G_A,
13_32953526_C_T, 13_32953556_G_T,
13_32953640_G_GA, 13_32953886_G_A,
13_32953974_C_G, 13_32954022_C_CA,
13_32954022_CA_C, 13_32954050_G_A,
13_32954147_TC T, 13_32954180_C_T,
13_32954222_C_T, 13_32954272_G_GA,
13_32954272_GA_G, 13_32968850_C_A,
13_32968863_C_G, 17_41197784_G_A,
17_41199658_A_T, 17_41203122_G_GC,
17_41209079_T_TG, 17_41209154_T_C,
17_41215362_TTTTC_T, 17_41215948_G_A,
17_41223097_G_A, 17_41223176_TG_T,
17_41223242_G_C, 17_41226411_G_A,
17_41226447_CTT_C, 17_41234421_CT_C,
17_41234451_G_A, 17_41243479_CTTGA_C, 17
41243533_C_A, 17_41243704_C_A,
17_41243800_C_A, 17_41243843_GTTTAC_G,
17_41244281_CA_C, 17_41244614_A_C,
17_41244865_GTT_G, 17_41244913_C_A,
17_41245161_G_GT, 17_41245203_CT_C,
17_41245330_CTT_C, 17_41245513_T_A,
17_41245586_CT_C, 17_41245603_C_A,
17_41245834_C_A, 17_41245888_C_A,
17_41246186_ACT_A, 17_41246197_AT_A,
17_41246278_CAG_C, 17_41246531_CT_C,
17_41246539_C_A, 17_41246723_G_GCCA-
CATGGCT, 17_41247864_ C_CT,
17_41247940_C_A, 17_41256203_TG_T,
17_41258504_A_C, 17_41267762_A_G,
17_41276044_ACT_A, and 17_41276048_TAA_T.

13. The method of claim 1, wherein the method further comprises:

determining that the test subject has HRD; and treating the cancer by administering a poly ADP ribose polymerase (PARP) inhibitor to the test subject.

14. The method of claim 13, wherein the PARP inhibitor is selected from the group consisting of olaparib, veliparib, rucaparib, niraparib, and talazoparib.

15. The method of claim 1, wherein the cancer is breast cancer.

16. The method of claim 1, wherein the cancer is ovarian cancer.

17. The method of claim 1, wherein the cancer is colorectal cancer.

18. The method of claim 1, wherein the classifier is a neural network, a support vector machine, a Naive Bayes classifier, a nearest neighbor classifier, a boosted trees classifier, a random forest classifier, a convolutional neural network classifier, a decision tree classifier, a regression classifier, or a clustering classifier.

19. The method of claim 1, wherein the classifier is a random forest classifier.

20. The method of claim 1, the method further comprising exome sequencing a plurality of cDNA molecules generated from the cancerous tissue of the subject to generate the first plurality of sequence reads.

21. The method of claim 1, the method further comprising exome sequencing a plurality of cDNA molecules generated from the non-cancerous tissue of the subject to generate the second plurality of sequence reads.

22. The method of claim 1, wherein the classifier determines that the probability that test subject has HRD is greater than fifty percent, and the method further comprises positively calling the test subject as HRD.

23. The method of claim 1, wherein the classifier determines that the probability that test subject has HRD is less than fifty percent, and the method further comprises calling the test subject as free of HRD.

24. A computer system comprising:

one or more processors; and a non-transitory computer-readable medium including computer-executable instructions that, when executed by the one or more processors, cause the processors to perform a method of determining a homologous recombination deficiency (HRD) status of a test subject afflicted with a cancer, the method comprising:

(A) generating, based on a first plurality of sequence reads of a first DNA sample from a cancerous tissue of the subject and a second plurality of sequence reads of a second DNA sample from a non-cancerous tissue of the subject, a set of genomic data for the test subject comprising:

(i) a heterozygosity status for a first plurality of DNA damage repair genes in the genome of the cancerous tissue of the subject, wherein the heterozygosity status derives from a count of a number of unique frameshift mutations or a number of unique truncating mutations detected in the first plurality of DNA damage repair genes in the genome of the cancerous tissue of the subject, (ii) a measure of the loss of heterozygosity, on a proportionate scale, across the genome of the cancerous tissue of the subject, (iii) a first measure of variant alleles detected in a second plurality of DNA damage repair genes in the genome of the cancerous tissue of the subject, wherein the first measure of variant alleles derives from a first count of a number of unique mutations associated with a loss of homologous recombination detected in the second plurality of DNA damage repair genes in the genome of the cancerous tissue of the subject, and (iv) a second measure of variant alleles detected in the second plurality of DNA damage repair genes in the genome of the non-cancerous tissue of the subject, wherein the second measure of variant alleles derives from a second count of a number of unique mutations associated with loss of homologous recombination detected in the second plurality of DNA damage repair genes in the genome of the cancerous tissue of the subject;

(B) determining a measure of tumor purity in the test subject using the first plurality of sequence reads;

(C) using the tumor purity in the test subject to verify that the tumor purity in the test subject satisfies a tumor purity threshold;

(D) applying a scaling construct to the set of genomic data thereby obtaining a scaled set of genomic data, wherein the scaling construct is derived from normalization of the set of genomic data from each subject in a training cohort of subjects, wherein the training cohort of subjects includes a first subset of subjects having HRD and a second subject of subjects free of HRD; and (E) inputting, after the using (C), the scaled set of genomic data into a classifier thereby determining a probability that the test subject has HRD.

25. A non-transitory computer-readable storage medium having stored thereon program code instructions that, when executed by a processor, cause the processor to perform a method of determining a homologous recombination deficiency (HRD) status of a test subject afflicted with a cancer, the method comprising:

(A) generating, based on a first plurality of sequence reads of a first DNA sample from a cancerous tissue of the subject and a second plurality of sequence reads of a second DNA sample from a non-cancerous tissue of the subject, a set of genomic data for the test subject comprising:

(i) a heterozygosity status for a first plurality of DNA damage repair genes in the genome of the cancerous tissue of the subject, wherein the heterozygosity status derives from a count of a number of unique frameshift mutations or a number of unique truncating mutations detected in the first plurality of DNA damage repair genes in the genome of the cancerous tissue of the subject, (ii) a measure of the loss of heterozygosity, on a proportionate scale, across the genome of the cancerous tissue of the subject, (iii) a first measure of variant alleles detected in a second plurality of DNA damage repair genes in the genome of the cancerous tissue of the subject, wherein the first measure of variant alleles derives from a first count of a number of unique mutations associated with a loss of homologous recombination detected in the second plurality of DNA damage repair genes in the genome of the cancerous tissue of the subject, and (iv) a second measure of variant alleles detected in the second plurality of DNA damage repair genes in the genome of the non-cancerous tissue of the subject, wherein the second measure of variant alleles derives from a second count of a number of unique mutations associated with loss of homologous recombination detected in the second plurality of DNA damage repair genes in the genome of the cancerous tissue of the subject:

(B) determining a measure of tumor purity in the test subject using the first plurality of sequence reads;

(C) using the tumor purity in the test subject to verify that the tumor purity in the test subject satisfies a tumor purity threshold;

(D) applying a scaling construct to the set of genomic data thereby obtaining a scaled set of genomic data, wherein the scaling construct is derived from normalization of the set of genomic data from each subject in a training cohort of subjects, wherein the training cohort of subjects includes a first subset of subjects having HRD and a second subject of subjects free of HRD; and (E) inputting, after the using (C), the scaled set of genomic data into a classifier thereby determining a probability that the test subject has HRD.

* * * * *

SEQUENCE LISTING

<160> NUMBER OF SEQ ID NOS: 2

<210> SEQ ID NO 1
<211> LENGTH: 12
<212> TYPE: DNA
<213> ORGANISM: Homo sapiens

<400> SEQUENCE: 1
atctacaaaa ag                                                    12

<210> SEQ ID NO 2
<211> LENGTH: 11
<212> TYPE: DNA
<213> ORGANISM: Homo sapiens

<400> SEQUENCE: 2
gccacatggc t                                                     11